(12) United States Patent
Kim et al.

(10) Patent No.: US 8,772,493 B2
(45) Date of Patent: Jul. 8, 2014

(54) COMPOUNDS HAVING AUDITORY PROTECTIVE EFFECT

(71) Applicants: Ajou University Industry-Academic Cooperation Foundation, Gyeonggi-do (KR); Korea Research Institute of Chemical Technology, Daejeon (KR)

(72) Inventors: Chul Ho Kim, Seoul (KR); Young Sik Jung, Daejeon (KR)

(73) Assignees: Ajou University Industry-Academic Cooperation Foundation, Gyeonggi-do (KR); Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 13/711,376

(22) Filed: Dec. 11, 2012

(65) Prior Publication Data

US 2013/0217881 A1    Aug. 22, 2013

Related U.S. Application Data

(63) Continuation-in-part of application No. PCT/KR2011/004297, filed on Jun. 13, 2011.

(30) Foreign Application Priority Data

Jun. 11, 2010  (KR) .................. 10-2010-0055536

(51) Int. Cl.
| | | |
|---|---|---|
| A01N 43/42 | (2006.01) | |
| A01N 43/40 | (2006.01) | |
| A61K 31/44 | (2006.01) | |
| A61K 31/445 | (2006.01) | |
| A61K 31/47 | (2006.01) | |
| C07D 215/00 | (2006.01) | |
| C07D 211/08 | (2006.01) | |
| C07D 401/00 | (2006.01) | |
| C07D 211/40 | (2006.01) | |
| C07D 419/00 | (2006.01) | |

(52) U.S. Cl.
USPC ........... 546/155; 546/158; 546/192; 546/219; 514/312; 514/299; 514/315; 514/328

(58) Field of Classification Search
USPC ........................................ 514/306; 546/155
See application file for complete search history.

(56) References Cited

FOREIGN PATENT DOCUMENTS

KR    10-0956576 B1    5/2010

OTHER PUBLICATIONS

Stadlbauer; Monatshefte fur Chemie 123, 617-636 (1992).*
Mukherjea; Expert Opin. Drug Discov., 2011, 6, 491-505.*
Hagmann; Journal of Medicinal Chemistry, 2008, vol. 51, 4359-4369.*
Kafka et al., "The first entry to pyrrolo[2,3-c]quinoline-2,4(3aH, 5H)-diones," Tetrahedron 64: 4387-4402, 2008.

(Continued)

*Primary Examiner* — John Mabry
*Assistant Examiner* — Daniel Carcanague
(74) *Attorney, Agent, or Firm* — Seed IP Law Group PLLC

(57) ABSTRACT

The present invention relates to a compound represented by formula 1 in the present specification or a pharmaceutically acceptable thereof, which inhibits an apoptosis mechanism of auditory hair cells for various ototoxicities leading to deafness, and protects the auditory organ and hearing, a method for preparation thereof, and a composition containing the same.

5 Claims, 23 Drawing Sheets

(56) References Cited

OTHER PUBLICATIONS

Klasek et al., "Unprecedented reactivity of 3-amino-1H,3H-quinoline-2,4-diones with urea: an efficient syntheis of 2,6-dihydroimidazo[1,5-c]quinazoline-3,5-diones," Tetrahedron 59: 1283-1288, 2003.

Pruckova et al., "Synthesis of 2-thioxoimidazolines via reaction of 1-unsubstituted 3-aminoquinoline-2,4-diones with isothiocyanates," Tetrahedron 65: 9103-9115, 2009.

* cited by examiner

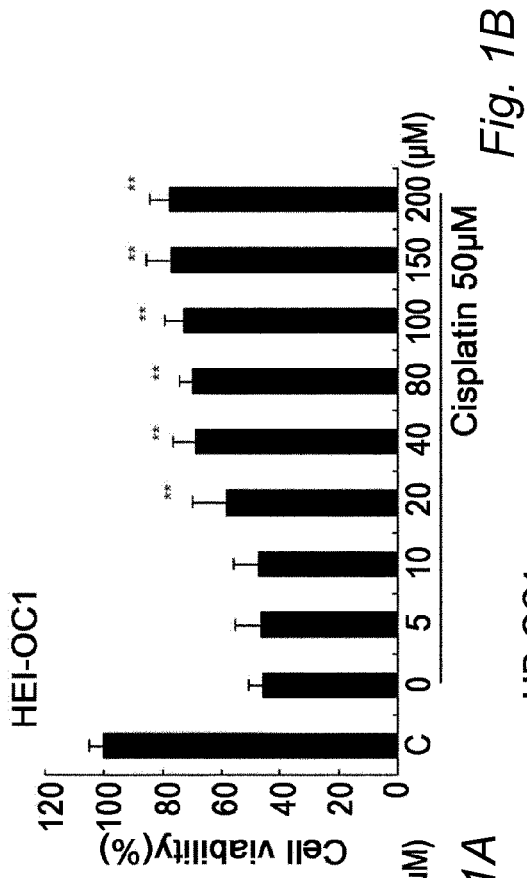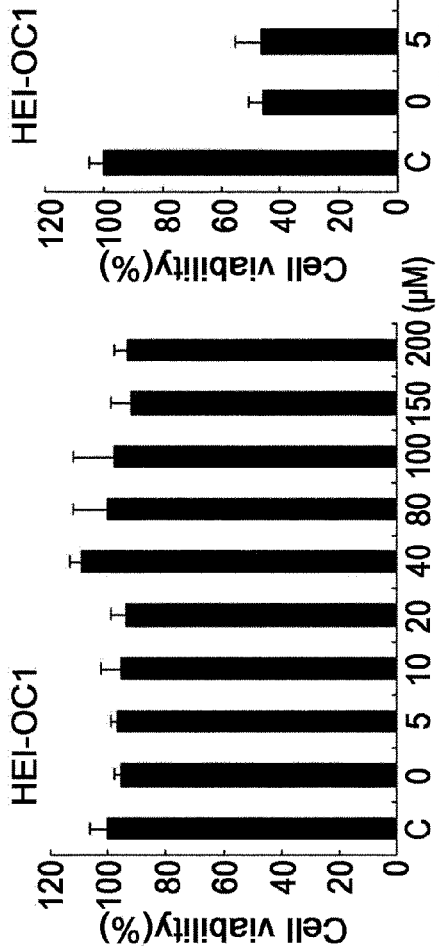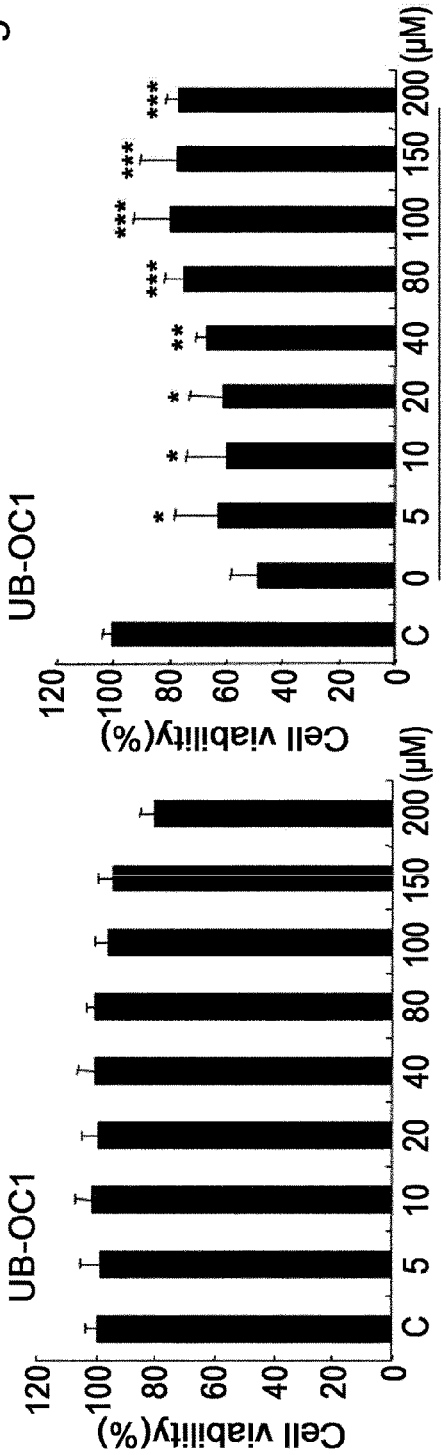
Fig. 1A
Fig. 1B
Fig. 1C
Fig. 1D

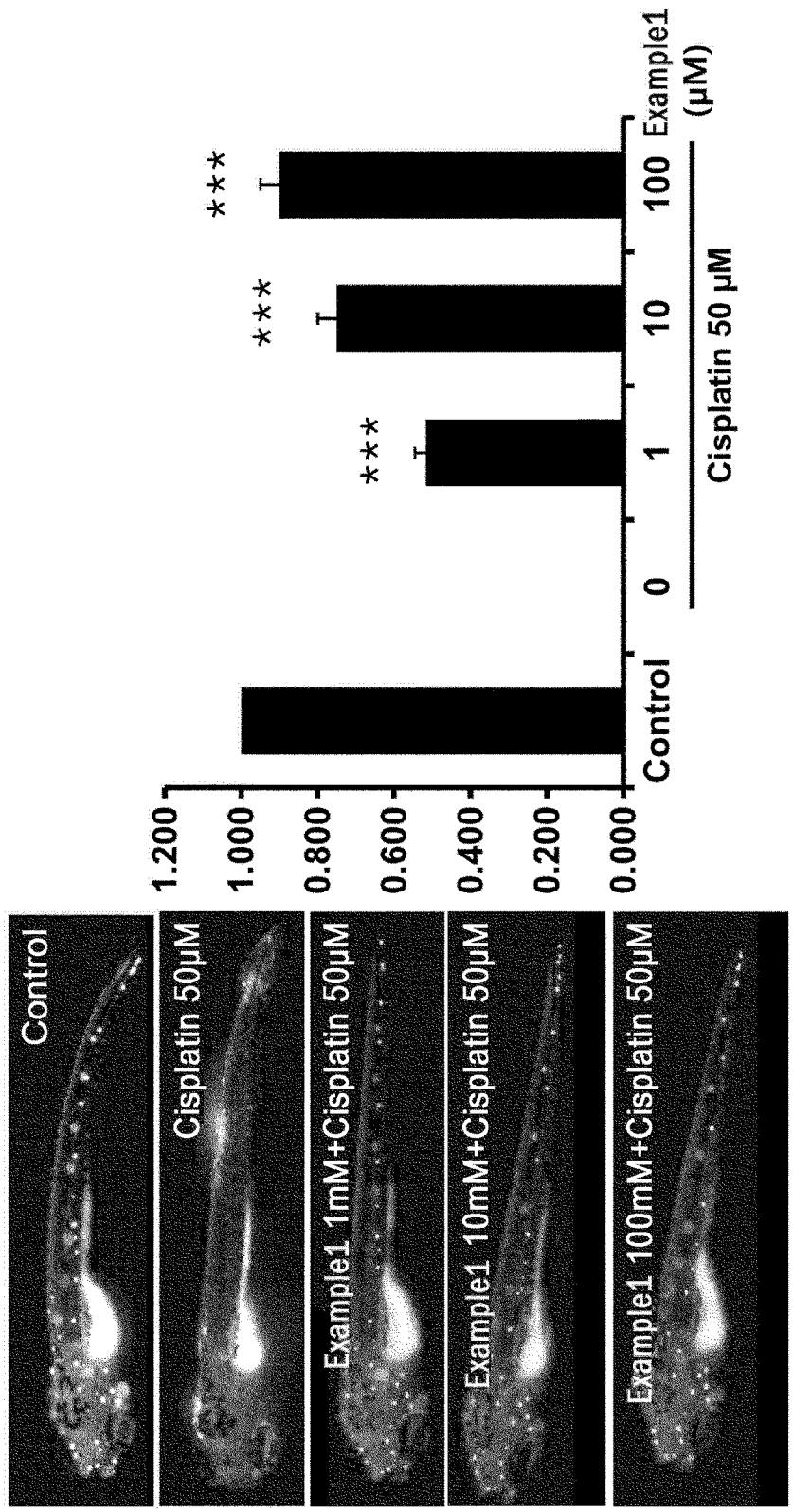

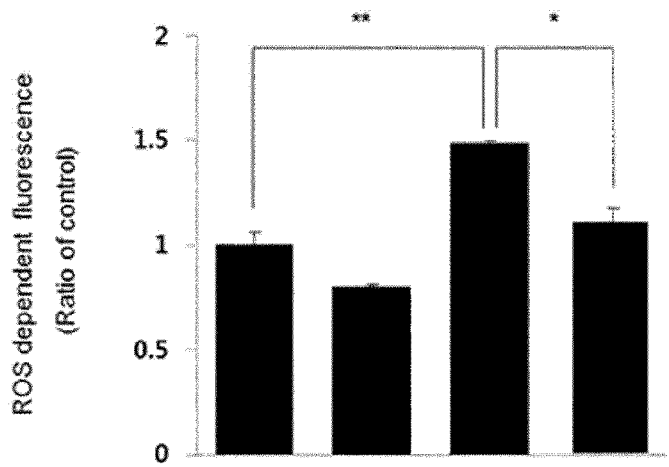
Fig. 15A
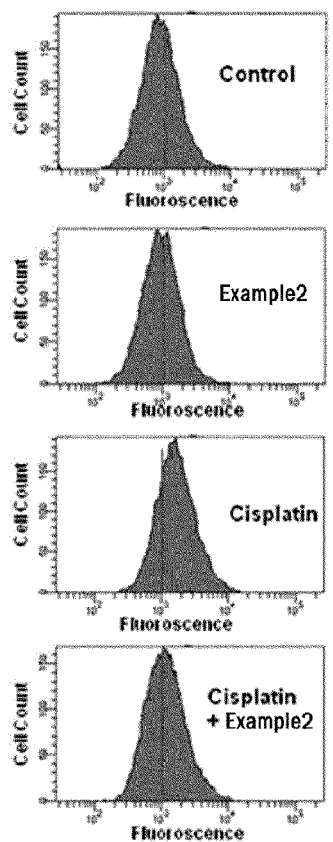
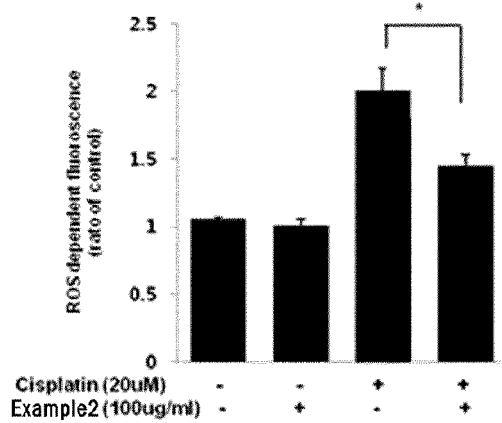
Fig. 15C
Fig. 15B

COMPOUNDS HAVING AUDITORY PROTECTIVE EFFECT

TECHNICAL FIELD

The present invention relates to a novel compound, which inhibits an apoptosis mechanism of auditory hair cells for various ototoxicities leading to deafness, and protects the auditory organ and hearing, a method for preparation thereof, and a composition containing the same.

BACKGROUND ART

Loss of the auditory sense as one of the senses of human body leads personally to disorders in daily life and socioeconomically to huge losses. Deafness not only induces hearing impairment, but also when a serious deafness breaks out before language acquisition, inhibits the normal language development to causes the problem of accompanying a speech impediment.

Patients suffering from moderate or more deafness, who are officially registered within the country as a hearing-impaired person, amount to about 150 thousands as of June, 2008 in Korea. Further, in view of the fact that the ratio of patients who were born with congenital, bilateral moderate deafness is 0.1%, the ratio of patients developing the acquired deafness is significantly higher. In addition, people with hearing and speech impairment amounts to 10% (Status of registered disabled people on 2002) of a total of registered disabled people in Korea, and thus, is a major cause of physical handicap. Loss of bilateral auditory sense is relevant to 100% loss rate of labor capacity according to McBride assessment of disablement and does not allow for a people to perform the normal economical activities, thereby resulting in an enormous socioeconomical loss. By way of example, it has been known that an astronomical amount of money would be required for a disabled people in the project, assuming an about 300-billion-won budget (Budget for disabled people as earmarked for disabled people by the Ministry of Health and Welfare of Korea for the year 2005—286.8-billion-won) supported by the government of Korea for assistance to a disabled people and the social indirect cost for a disabled people.

Further, with the geometrical rise in aged population, presbycusis as recently emphasized, together with hypertension and degenerative arthritis is one of three age-related diseases, and has been known as a disease having a high prevalence rate which is found in 25-40% of the number of people over sixty-five in Korea. According to the 2000' data of the National Statistical Office of Korea, the number of people over sixty exceeds 5 millions, and thus the potential support ratio amounts to about 11%, which constitutes an object of public concern. In addition, a disease of sensory organs, such as auditory sense, of the elderly people is also an important element limiting social activities of elderly man. Thus, it is urgently required to study degenerative sensory diseases and to develop a therapeutic agent thereof.

Among drugs used for patients suffering from various diseases including cancers, many drugs exhibit the ototoxicity and can be represented by aminoglycoside-based antibiotics and anticancer agents such as cisplatin, etc. Their typical side-effects include nephrotoxicity and ototoxicity. As compared to the nephrotoxicity, the ototoxicity irreversibly leads to a bilateral permanent loss of hearing and vestibular function in many cases, and the prevalence rate of ototoxicity is high to reach 7.5% as it has been reported to be 0.6-30% for cochlea toxicity and 0-75% for vestibular toxicity depending on the reporters in Korea.

Meanwhile, in addition to presbycusis and ototoxic deafness the common cause of acquired deafness is noise deafness, which is recently on the rise. According to the data reported in Korea in the year 1995, among a total of 782,274 cases of the special health examination for workers under harmful environments the cases of special examination for noise was the largest as 364,244 cases (44.3%), and among a total of 5,942 cases suffering from occupational diseases developed in the year 1992 the number of patients diagnosed as noise deafness was 3,345 beyond the half thereof. In addition, according to the result of health examination practiced in Korea in the year 1999, among a total of 2,713,240 workers from 115,761 working places 1,794 cases were confirmatively diagnosed as an occupational disease, wherein 1,056 cases to be 58.9% thereof were identified as noise deafness. Thus, it can be noted that among the occupational diseases a ratio of noise deafness is very high. Therefore, the noise has emerged as the problem which should be solved with having an overriding concern.

It is considered that if the mechanism of apoptosis of auditory organs due to various causes (drugs, radiation, noise, environmental pollution—electromagnetic wave, etc.) would be revealed and a material and gene, which can control of such apoptosis of auditory organs would be found, deafness originated from various causes or unknown cause will be prevented or treated. Recently, as the study of inner ear hair cell damage related to deafness has been actively progressed, a death of auditory hair cell due to free oxygen radical (reactive oxygen species, ROS) has been reported as the main cause of deafness, and the search and development of an auditory protective agent related thereto is being actively made.

Technical Problem

The present invention is contrived by the above-mentioned need. The purpose of the present invention is to provide a compound that protects hearing by inhibiting apoptosis of auditory hair cells, and protects the auditory organ and hearing, a method for preparation thereof, and a composition comprising the same.

Technical Solution

To achieve the above purposes, the present invention provides a compound represented by the following formula 1:

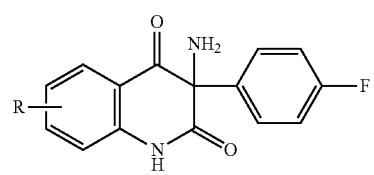

[Formula 1]

or a pharmaceutically acceptable salt thereof, wherein R is hydrogen or halogen. In this formula, R means a substituent substituted on benzene ring of quinolin-2,4(1H,3H)-dione Preferably, said R is hydrogen or F.

In addition, the compound represented by the above formula 1 is preferably:
1) 3-amino-3-(4-fluorophenyl)quinolin-2,4(1H,3H)-dione, or
2) 3-amino-5-fluoro-3-(4-fluorophenyl)quinolin-2,4(1H,3H)-dione.

In addition, as shown in the following reaction scheme 1, the present invention provides a method for preparation of the compound represented by formula 1, which comprises:

1) the step of reacting a compound represented by formula 2 with 2-(4-fluorophenyl)acetyl chloride to prepare a compound represented by formula 3;

2) the step of reacting the compound represented by formula 3 with NaH to prepare a compound represented by formula 4;

3) the step of reacting the compound represented by formula 4 with $SO_2Cl_2$ to prepare a compound represented by formula 5;

4) the step of reacting the compound represented by formula 5 with NaH to prepare a compound represented by formula 6; and 5) the step of reacting the compound represented by formula 6 with $H_2$ to prepare the compound represented by formula 1.

[Reaction Scheme 1]

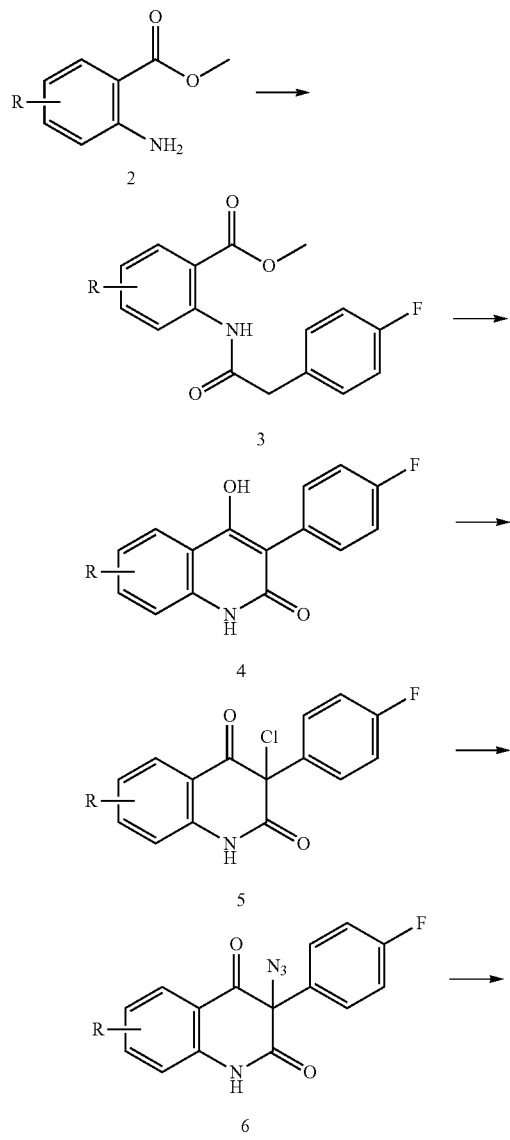

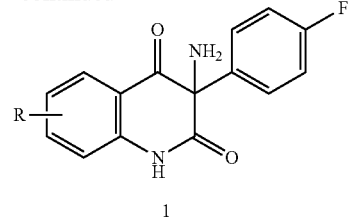

Said step 1 is a substitution reaction of 2-(4-fluorophenyl)-acetyl, wherein 2-(4-fluorophenyl)-acetyl is preferably reacted with DMAP (4-dimethylaminopyridine). In this reaction, $CH_2Cl_2$ may be used as a solvent.

Said step 2 is a cyclization, wherein DMF (dimethylformamide) may be used as a solvent.

Said step 3 is a ketonization, wherein 1,4-dioxane may be used as a solvent.

Said step 4 is a substitution reaction of Cl with $N_3$, wherein DMF may be used as a solvent.

Said step 5 is a substitution reaction of $N_3$ with $NH_2$, wherein the reaction is preferably carried out under Pd/C catalyst, and MeOH may be used as a solvent.

Further, the present invention provides a pharmaceutical composition for auditory protection, which comprises the compound represented by the above formula 1, or the pharmaceutically acceptable salt thereof. In addition, the present invention provides a pharmaceutical composition comprising the compound represented by the above formula 1, or the pharmaceutically acceptable salt thereof, for use in auditory protection. In addition, the present invention provides a use of the pharmaceutical composition comprising the compound represented by the above formula 1, or the pharmaceutically acceptable salt thereof for use in preparing a medicine for auditory protection.

Said composition is characterized in that it has an activity for inhibiting apoptosis of auditory cells, and thus, can protect the auditory sense. In addition, said composition is characterized in that it can protect auditory sense from ototoxic stimulation. Said ototoxic stimulation can be caused by anti-cancer agents, antibiotics, radiation, electromagnetic wave or noise.

The above-mentioned anti-cancer agents or antibiotics can include cisplatin, carboplatin, nitrogen mustard, vincristine, amikacin, azithromycin, capreomycin, chloramphenicol, dibekacin, dihydrostreptomycin, etiomycin, erythromycin, gentamicin, metronidizole, neomycin, netilmicin, polymyxin B, streptomycin, tobramycin, vancomycin, proxin, macrolide, lasix (furosemide), bumex (bumetanide), edecrin (ethacrynic acid), piretanide, quinidex, atabrine, plaquenil, quinine sulfate, mefloquine (lariam), chloroquine, or aspirin.

In the pharmaceutical composition, the effective amount of the compound represented by the above formula 1 or the pharmaceutically acceptable salt thereof is preferably, but not limited to, the range of 5 μM to 400 μM.

The compound of the present invention can be provided in the form of a pharmaceutically acceptable salt. As the salts, acid addition salts formed by pharmaceutically acceptable free acids are useful. The compound represented by the above formula 1 can form the pharmaceutically acceptable acid addition salts thereof according to conventional methods commonly used in the relevant technical field. As the free acid organic acids and inorganic acids can be used, wherein hydrochloric acid, hydrobromic acid, sulfuric acid, phosphoric acid, etc. can be used as the inorganic acid, and citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, galacturonic acid, embonic acid, glutamic acid or aspartic acid can be used as the organic acid.

In another aspect, a suitable salt is base addition salts such as alkali metal salts, for example, sodium or potassium salt, alkaline earth metal salts, for example, calcium or magnesium salt, or organic amine salts, for example, triethylamine salt.

The pharmaceutical composition of the present invention and the dosage form thereof can further comprise one or more additional active ingredients. Consequently, the pharmaceutical composition of the present invention and the dosage form thereof can comprise the active ingredients disclosed in the present specification.

The single unit dosage form of the present invention is useful for oral, mucosal (e.g. nasal, sublingual, vaginal, buccal, or rectal), parenteral (e.g. subcutaneous, intravenous, bolus injection, intramuscular or intra-arterial), topical (e.g. eye), transdermal or transcutaneous administration to patients. Further, for preparing the dosage form excipients, stabilizers, binders, fillers, disintegrators, lubricants, etc. can be included.

Further, the present invention provides a health food composition or a feed composition for auditory protection which comprises the compound represented by the above formula 1, or the pharmaceutically acceptable salt thereof.

The food or feed for auditory protection characterized in that it contains the compound of the present invention as an active ingredient can be generally prepared by adding the compound of the present invention to the food or feed. Said food or feed composition is used for auditory protection as the health foods or functional foods.

The food or feed composition of the present invention can be prepared using the general method for preparing foods or feeds, except that the composition of the present invention, and if necessary, other effective components are added.

Further, said food or feed composition can be processes according to the general method for processing foods or feeds, for example, molding and granulation. The processing methods can include granulation methods including fluidized bed granulation, stirring granulation, extruding granulation, motorized granulation, air current granulation, compression molding granulation, crushing granulation, spraying granulation, jet granulation, etc., coating methods including pan coating, fluidized bed coating, dry coating, etc., bulking methods including puffing dry, excessive steaming method, foam matting method, microwave heating method, etc., and the like.

The amount of the compound of the present invention added to the food or feed composition of the present invention is not specifically limited if the food or feed composition of the present invention has the activity for auditory protection, but is added to include, for example, 0.01 to 50 wt %, preferably 0.1 to 10 wt %.

The foods produced by adding the compound of the present invention can include, for example, health food, health beverage, juices, soft drinks, soups, teas, yogurt drinks, diary products such as fermented milk, ice cakes, butter, cheese, yogurt, processed milk, dried skim milk, etc., meat products such as ham, sausage, hamburger, etc., fish combined products, egg products such as folded egg, egg tofu, etc., biscuits such as cookie, jelly, snacks, chewing gums, etc., breads, noodles, kimchi, smoked products, dried products, seafood boiled in soy sauce, seasonings, and the like.

The feed composition of the present invention can be manufactured by appropriately combining the compound of the present invention into the raw feed materials. The raw feed materials can include grains, wine lees and bran, vegetable oil cakes, animal raw feed materials, other raw feed materials, purified materials, etc.

Advantageous Effects

The compound of the present invention or its pharmaceutically acceptable salts, or the composition comprising the same exhibits an effect as the auditory protective agent, particularly a superior effect of inhibiting apoptosis of auditory cells caused by various ototoxic stimulations (anti-cancer agents or radiation, or the combined use thereof).

DESCRIPTION OF DRAWINGS

FIGS. 1A-1D show the results of MTT assay for the effect of the compound of Example 1 to inhibit apoptosis of auditory cells induced by anti-cancer agent, cisplatin, as the ototoxic material.

FIGS. 12A-12B are photographs obtained from fluorescence microscopy for the auditory protective effect using zebrafish model for the compound of Example 1.

FIGS. 15A-15C is the effect of the compound of the present invention on cisplatin-induced ROS generation in HEI-OC1 cells.

BEST MODE

Figure 2A:
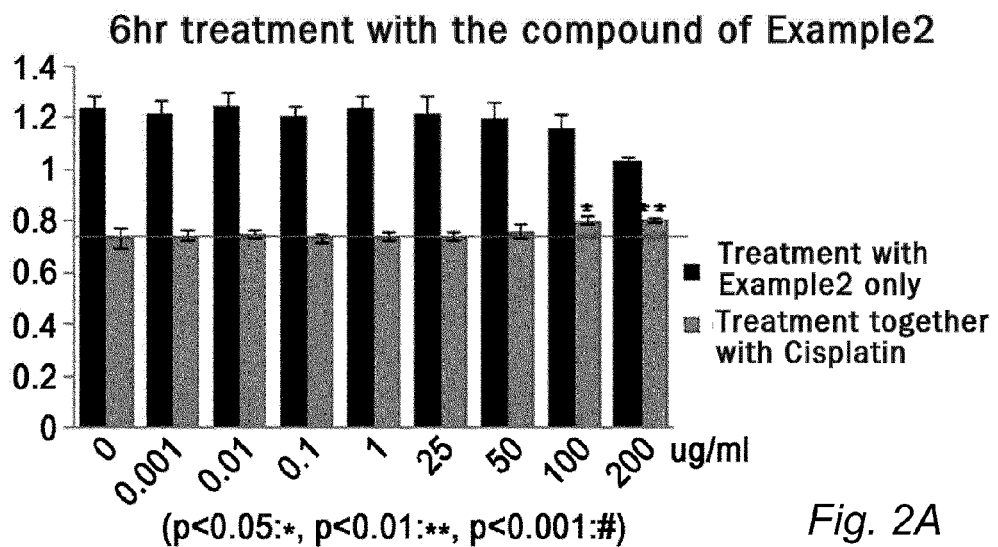
FIGS. 2A-2B show the results of MTT assay for the effect of the compound of Example 2 to inhibit apoptosis of auditory cells induced by anti-cancer agent, cisplatin, as the ototoxic material.

Hereinafter, the present invention will be more specifically illustrated by the following non-limiting Examples. However, the following Examples are intended only to explain the present invention, and the scope of the present invention is not interpreted as being limited to the following Examples.

Example 1

Preparation of 3-amino-3-(4-fluorophenyl)quinolin-2,4(1H,3H)-dione

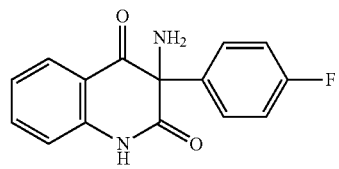 [SMILES: NC1(c2ccc(F)cc2)C(=O)Nc2ccccc2C1=O]

First, 2-amino-benzoic acid methyl ester (1.00 g, 6.61 mmol) was dissolved in purified $CH_2Cl_2$, and DMAP (0.04 g, 0.33 mmol) was added thereto at 0° C. Then, the mixture was added to the reaction vessel containing (4-fluorophenyl)-acetyl chloride produced from reaction of (4-fluoro-phenyl)-acetic acid (1.53 g, 9.90 mmol) with $SOCl_2$, and then reacted at normal temperature for 10 hours. After adding cold sodium bicarbonate solution containing ice, the reaction mixture was extracted with $CH_2Cl_2$, and then concentrated under reduced pressure to obtain 1.50 g (79%) of the compound 2-[2-(4-fluorophenyl)-acetylamino]-benzoic acid methyl ester as the solid.

Next, cyclization reaction was carried out using NaH to obtain 3-(4-fluoro-phenyl)-4-hydroxy-1H-quinolin-2-one and 3-chloro-3-(4-fluoro-phenyl)-1H-quinolin-2,4-dione in the yield of 90%, and then, chlorination (Yield 88%) and azidation were carried out to obtain 3-azido-3-(4-fluorophenyl)-1H-quinolin-2,4-dione (Yield 88%).

The azido compound (0.10 g) obtained above was dissolved in purified MeOH, and then 10% Pd/C (0.01 g, 10 wt %) was added. The mixture was then reacted together for one hour while injecting hydrogen by means of a balloon. The reaction solution was filtered through celite, and the filtrate was then concentrated under reduced pressure. The residue was purified with silica gel column chromatography to obtain the title compound (0.08 g, 87%) as the solid.

$^1$H NMR (300 MHz, $CDCl_3$) d 2.67 (br s, 2H, NH2), 6.91-7.01 (m, 3H, ArH), 7.09 (t, J=7.5 Hz, 1H, ArH), 7.38~7.49 (m, 3H, ArH), 7.84 (dd, J=7.8, 1.4 Hz, 1H, ArH), 10.27 (br s, 1H, NH)

$^{13}$C NMR (75 MHz, $CDCl_3$) d 70.8, 115.9, 116.2, 116.6, 119.4, 124.0, 127.7, 127.8, 128.1, 136.2, 139.9, 161.0, 164.3, 173.3, 193.7. mp 187-188. Mass (EI) $C_{15}H_{11}FN_2O_2$ ([M$^+$] 270)

Example 2

Preparation of 3-amino-5-fluoro-3-(4-fluorophenyl)quinolin-2,4(1H,3H)-dione

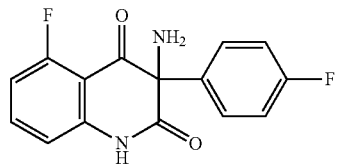 [SMILES: NC1(c2ccc(F)cc2)C(=O)Nc2cccc(F)c2C1=O]

First, 2-amino-6-fluoro-benzoic acid methyl ester (1.00 g, 5.91 mmol) was dissolved in purified $CH_2Cl_2$, and after adding DMAP (0.04 g, 0.30 mmol) and (4-fluoro-phenyl)-acetyl chloride (1.22 g, 6.50 mmol) at 0° C., reacted together at normal temperature for 10 hours. After adding cold sodium bicarbonate solution containing ice, the reaction mixture was extracted with $CH_2Cl_2$, washed with distilled water, dried with $MgSO_4$, and then concentrated under reduced pressure to obtain crude 2-fluoro-6-[2-(4-fluoro-phenyl)-acetylamino]-benzoic acid methyl ester (1.20 g, 61%) as the solid.

$^1$H NMR (300 MHz, $CDCl_3$) d 3.71 (s, 2H, COCH$_2$Ph), 3.88 (s, 3H, OCH$_3$), 6.79~6.85 (m, 1H, ArH), 7.07 (t, J=8.7 Hz, ArH), 7.30~7.44 (m, 5H, ArH), 8.37 (d, J=8.40, 1H, ArH), 10.46 (br s, 1H, NH).

Next, 2-fluoro-6-phenylacetylamino-benzoic acid methyl ester (1.00 g, 3.27 mmol) was dissolved in purified DMF, and then 60% NaH (0.20 g, 4.91 mmol) was added thereto at 0° C. Then, the mixture was slowly raised to normal temperature, and stirred for one hour. The reaction mixture was acidified with cold 2 N HCl containing ice to obtain the solid product, which was then filtered to obtain crude 5-fluoro-3-(4-fluorophenyl)-4-hydroxy-1H-quinolin-2-one (0.70 g, 78%) as the solid.

$^1$H NMR (200 MHz, DMSO-d$_6$) δ 6.88~6.98 (m, 1H, ArH), 7.10~7.38 (m, 3H, ArH), 7.40~7.53 (m, 3H, ArH), 9.76 (br s, 1H, OH), 11.69 (br s, 1H, NH).

Then, 5-fluoro-4-hydroxy-3-phenyl-1H-quinolin-2-one (1.00 g, 3.66 mmol) was dissolved in 1,4-dioxane, and SO$_2$Cl$_2$ (0.40 ml, 4.00 mmol) was slowly added thereto at 0° C. The mixture was slowly raised to normal temperature and stirred for one hour. The reaction mixture was poured into cold water containing ice, and then extracted with EtOAc. The organic layer was washed two times with water, dried with MgSO$_4$, and then concentrated under reduced pressure to obtain 3-chloro-5-fluoro-3-(4-fluoro-phenyl)-1H-quinolin-2,4-dione (1.03 g, 91%) as the solid.

$^1$H NMR (200 MHz, DMSO-d$_6$) δ 6.89~6.98 (m, 2H, ArH), 7.20~7.29 (m, 2H, ArH), 7.39~7.47 (m, 2H, ArH), 7.55~7.66 (m, 1H, ArH), 11.61 (br s, 1H, NH).

Then, 3-chloro-5-fluoro-3-phenyl-1H-quinolin-2,4-dione (1.00 g, 3.25 mmol) was dissolved in purified DMF, and then sodium azide (0.42 g, 6.50 mmol) was added thereto at 0° C. The mixture was then stirred at normal temperature for 2 hours. The reaction mixture was extracted with ice-water and Et$_2$O. The extracted organic layer was dried with MgSO$_4$, and then concentrated under reduced pressure. The residue was then subjected to silica gel column chromatography to obtain 3-azido-5-fluoro-3-(4-fluoro-phenyl)-1H-quinolin-2,4-dione (0.98 g, 96%) as the solid.

$^1$H NMR (200 MHz, CD$_3$OD) δ 6.81~6.90 (m, 2H, ArH), 7.18~7.29 (m, 2H, ArH), 7.46~7.60 (m, 3H, ArH).

Then, 3-azido-5-fluoro-3-phenyl-1H-quinolin-2,4-dione (1.00 g, 3.18 mmol) was dissolved in purified MeOH, and then 10% Pd/C (0.1 g, 10 wt %) was added. The mixture was then reacted together for one hour while injecting hydrogen by means of a balloon. The reaction solution was filtered through celite, and the filtrate was then concentrated under reduced pressure and recrystallized (EtOAc) to obtain the title compound (0.41 g, 45%) as the solid.

$^1$H NMR (300 MHz, CDCl$_3$) d 2.50 (br s, 2H, NH$_2$), 6.76-6.80 (m, 2H, ArH), 6.95-7.01 (m, 2H, ArH), 7.36-7.44 (m, 3H, ArH), 9.87 (s, 1H, NH).

Experiment 1

MTT Assay

HEI-OC1 and UB-OC1 as auditory cells were subjected to MTT assay. Auditory cell lines were seeded on a 96-well plate in the ratio of $2\times10^3$ cells/well, and then cultured in an incubator under the condition of 37° C., 5% CO$_2$ for 2 days. The compounds of Examples 1 and 2 were used at various concentrations with operating 5 runs for each sample, and then cultured in the incubator for 16 hours. The plate was treated with 1 mg/ml MTT solution per well, and then cultured in the incubator for 4 hours. Then, 100 μl DMSO per well was used to dissolve formazan, and the optical density of formazan as dissolved was measured at 540 nm.

Experiment 2

TUNEL Assay

The apoptosis of HEI-OC1 treated with the compounds of Example 1 and compound of Example 2 was demonstrated in the in situ cell death detection kit, POD (Roche, Germany), using TUNEL assay. $3\times10^5$ cells were seeded on the 6-well, incubated, then starved for 24 hours, and treated with the drug of the present invention by conditions, and then incubated for 24 hours. The cells were fixed with addition of 4% paraformaldehyde at normal temperature for 30 minutes, then washed two times with PBS, and treated with the permeablilization solution comprising 0.1% Triton X-100 at normal temperature for 10 minutes. The cells were washed again two times with PBS, and after adding terminal deoxynucleotidyl transferase (TDT) and nucleotide mixture, incubated for one hour with blocking out the light at 37° C. After washing two times with PBS, the apoptosis of cells was examined under fluorescence microscope. For control staining of cells without apoptosis, 4,6-diamino-2-phenylindole (DAPI, Sigma) solution was used. The stained cells were analyzed using a fluorescence microscope (Carl Zeiss, Oberkochen, Germany). TUNEL-positive cells were manually counted under a 200× magnification field in triplicate.

Experiment 3

FACScan with Annexin-V and PI Double Staining

The degree of apoptosis was analyzed with Annexin V-FITC Apoptosis Detection kit I (BD Biosciences, San Diego, Calif.). $3\times10^5$ cells were seeded on 60 mm dish, incubated, then starved for 24 hours, and treated with the compounds of Examples 1 and 2 by conditions and incubated for 24 hours. After removing the culture solution, the cells were washed two times with PBS, and suspended in the binding buffer in the ratio of $1\times10^6$ cells/ml. 100 μl of this solution was transferred to 5 ml tube, and after addition of 5 μl of Annexin V-FITC to the tube, well mixed together, and then reacted for about 15 minutes in the dark place. Then, 400 μl of the binding buffer was added, and the cells were counted until 10,000 cells were on Becton Dicki nson FACSscan (Lysis II Ver. 1.0). The degree of apoptosis was measured depending on the expression of Annexin V-FITC from the result of FACScan flowcytometry. In addition, the degree of apoptosis was also measured under fluorescence microscope.

Experiment 4

Cell Cycle Analysis Using FACScan

HEI-OC1 cells were incubated overnight on the six-well plate in the ratio of $10^6$ cells/ml, and then treated with cisplatin and the compound of Example 1. The cells were treated with trypsin, washed with PBS, and then stained with a dye (5 mg/ml propidium iodide, 20 mg/ml RNase A) in a dark room at normal temperature for 15 minutes. The stained cells were analyzed with a flow cytometry cell sorter (Becton Dickinson).

Experiment 5

Measurement of Mitochondrial Membrane Potential (MMP)

The mitochondrial membrane potential (MMP) was measured using 5,5V,6,6V-tetrachloro-1,1V,3,3V-tetraethylbenzimidazolcarbocyanine iodide (JC-1; Molecular Probes) as a lipophilic cationic probe.

JC-1 is a fluorescent dye which is accumulated by mitochondria in its inside. If the function of mitochondria is normal, MMP is high and mitochondria are predominantly red. Then, if mitochondria are damaged, MMP is reduced and mitochondria are changed into green. Taking advantage of such property, HEI-OC1 was treated with cisplatin and the compounds of Examples 1 and 2, and then a change in MMP was measured with flow cytometry and fluorescence microscopy.

Experiment 6

Western Blotting

Auditory cell line, HEI-OC1 was washed with phosphate buffered saline (PBS), and then homogenized by adding to RIPA (RadioImmunoPrecipitation) buffer 1 ml (150 mM NaCl, 1% NP-40, 50 mM Tris (pH 8.0), 1 mM EDTA, 0.5% Deoxycholate) comprising proteolysis inhibitor (100 µg/ml phenylmethylsulfonyl fluoride, 1 µg/µl leupeptin). The homogenate was centrifuged with 15,000 rpm for 10 minutes, and the supernatant was subjected to Western blot analysis. The content of protein was measured by means of Bio-Rad protein assay (Bio-Rad, Hercules, Calif. USA). 20 µg of protein per well was separated with sodium dodesyl sulfate (SDS)-polyacrylamide gel electrophoresis (PAGE), transferred to nitrocellulose filter (Amersham, Arlington Heights, Ill. USA), and then reacted overnight with anti c-Met antibody at 4° C. On the next day, the filter was washed with Tris buffered saline (TBS) solution containing 0.1% Tween-20, reacted with peroxidase-conjugated donkey anti-rabbit antibody (Amersham) and donkey anti-mouse antibody (Amersham), respectively, and then examined with X-ray film using enhanced chemiluminescence detection system (ECL, Amersham).

Experiment 7

Analysis of Drug Toxicity in Zebrafish and Effect on Zebrafish Embryos

To identify the drug toxicity of the compound of the present invention, zebrafish (Danio rerio) embryo was treated with the compound of Example 1 by concentrations (0, 50, 100, 150, 200, 400 µM), and then cultured in the incubator at 28.5° C. for one hour, washed three times with fresh 0.3× Danieu's Solution, and then cultured at 28.5° C. for 3 hours. The embryotoxicity was identified by examining the hatching rate, organogenesis, development, etc. of embryo under a microscope (AXIO vert 200, Carl zeiss, Gottingen, Germany), and the survival rate of embryo was determined depending on whether the cardiac contractility of embryo is present or absent.

Further, to determine the general toxicity of the compound of Example 1, the influence of the compound of Example 1 on embryos of zebrafish were tested. One female and two male sexually mature zebrafish were maintained for a 14 h light/10 h dark photoperiod. Several rectangular mesh wire boxes were placed at the bottom of the aquaria to collect the eggs the following morning. The eggs were pre-treated with the compound of Example 1 (100 µg/ml) for 1 hr, after then the eggs were washed twice with sea salt 1×. Subsequently, the eggs were seeded in 96-well plates at densities of 10 eggs/well in 1 ml sea salt 1× and treated with various concentrations of the compound of Example 1 (0, 50, 100 µg/ml) and cisplatin (50 µM) simultaneously for 24 h. After three washes with sea salt 1×, the zebrafish eggs were observed under a microscope.

Experiment 8

Observation of Zebrafish Neuromast Using Fluorescent Microscope

When embryo of zebrafish (Danio rerio) wild type is on the 4$^{th}$ day, the drugs (compounds of Examples 1 and 2) were added to 2 ml of embryo media in 6 well, and then 5 embryos were added to each group and reacted with the drug in the incubator maintained at 28.5° C. for one hour. After reaction, embryos were washed three times with embryo media, and then placed in clean embryo media for 3 hours. After 3 hours, 2 of Yo-Pro-1 (molecular probes, Oregon U.S.A) was added to embryo media, and then reacted for one hour in the place with blocking the light. After reaction, embryos were washed again three times with clean embryo media, and anesthetized with 8 µg/ml of MS222 (3-aminobenzoic aid ethyl ester, methanesulfonate salt, Sigma Chemical CO, St Louis, U.S.A) anesthetic. Then, the fluorescent expression of neuromast, which exhibits the auditory function in zebrafish, was observed using a fluorescent microscope.

Experiment 9

Scanning Electron Microscopy of Zebrafish Neuromast

Zebrafish embryos (dpf 4) treated with cisplatin and the compound of Example 1 under various conditions were dehydrated with ethanol solution (25, 50, 70, 80, 95%) and then, the samples were treated with 25%, 50%, 75%, and 100% isoamyl acetate. They were dried with a drier, treated with an evaporator (MED010; Baltec, Hudson, N.H.), and then observed using a scanning microscope (JSM-6700F JEOL, Tokyo, Japan).

Experiment 10

Transmission Electron Microscopy of Zebrafish Neuromast

Zebrafish (Danio rerio) embryos (dpf 4) treated with cisplatin and the compound of Example 1 under various conditions were treated with 4% glutaraldehyde in 0.1M sodium cacodylate (pH 7.4) and 0.001% $CaCl_2$ for one hour, dehydrated with ethanol stepwise, and then treated with Spurr's epoxy resin through propylene oxide. Larvae were cut in the direction from head to tail, sliced to a thickness of 2, and then stained with 1% toluidine blue. They were divided into ultrathin sections (90 nm) using Ultracut S microtome (Leica, Wetzlar, Germany), mounted on 200-mesh Athene thin bargrids, treated with uranyl acetate and lead citrate, and then observed using s transmission electron microscope (EM 902A Carl Zeiss).

Experiment 11

Measurement of Intracellular ROS Generation

Intracellular generation of ROS was quantified using 5-(and 6)-carboxyl-20,70-dichlorodihydro fluorescein diacetate (DCFDA; Molecular Probes, Eugene, Oreg., USA). For the assay, HEI-OC1 cells were cultured overnight on 6-well plates and then treated with 50 µM cisplatin in the presence or absence of the compound of Example 1 and the compound of Example 2 (100 µg/ml) for 16 h. ROS generation at various time points was checked and the amount of ROS generation was the highest at 16 h. Therefore, 16 h as the time point for ROS detection was chosen for subsequent experiments. Cells were incubated in the dark with 10 µM DCFDA in serum-free medium for 10 min at 33° C. The oxidative burst (hydrogen peroxide, $H_2O_2$) was detected using a FACScan flow cytom-

Experiment 12

Tissue TUNEL in Zebrafish

To detect the apoptotic cells in the embryos, TUNEL assay was employed. The larvae were exposed to egg water with cisplatin (50 μM) plus the compound of Example 1 (50 or 100 μg/ml) for 24 h. Thereafter, the larvae were washed with PBS and fixed in 4% paraformaldehyde with 0.1% Tween 20 at room temperature for 24 h. The fixed embryos were then dehydrated, rehydrated, and treated with 60 μg/ml protease kinase (Invitrogen, USA) for 10 min. After the protease kinase treatment, the embryos were fixed in 4% paraformaldehyde in PBS with 0.1% Tween 20 again. The TUNEL staining was achieved by using an in situ apoptosis detection kit. The fixed embryos were immersed in the permeabilization buffer for 30 min on ice. The apoptotic cells were labeled by staining the embryos in a mixture of Terminal Deoxynucleotidyl Transferase (TdT) enzyme and labeling safe buffer containing Fluorescein labeled-2'-Deoxyuridine, 5'-Triphosphate, FITC-dUTP in the ratio of 1 to 9. The embryos were then incubated in a 37° C. humidified chamber for 120 min. The embryos were finally washed thoroughly by PBS in 0.1% Tween 20. The apoptotic signals were captured by a fluorescence microscope (Carl Zeiss, Oberkochen, Germany).

Experiment 13

Measurement of Brainstem Evoked Potential Hearing in Rat

Rats were anesthetized with a mixed anesthetic of 1:1 zoletil and rompun, and then subjected to the examination of brainstem evoked potential hearing. The examination of brainstem evoked potential hearing was conducted by lying rats with a supine position in a specially-manufactured, soundproof room, which is dark and electrically blocked. The stimulus sound was measured by lowering 13 times/sec of the alternating click sound from the strength of 75 dB HL at the ratio of 5 dB per step. The hearing threshold was defined to be a strength at which the normal wave form I is assumed on the basis of the wave form I, the frequency filter of click sound was controlled to 100-3000 Hz, and the number of total stimulus sound was 1,024.

After administration of cisplatin, rats were divided into the group with the combined use of the compound of Example 1 and the control group without administration of the compound of Example 1. In the neat group, the examination of brainstem evoked potential hearing was conducted, and then 2 mM of the compound of Example 1, or DMSO for the control group was administered. The drug was administered inside eardrum of rats with a 26 gage needle. The brainstem evoked potential hearing was measured a total of three times on days 1, 3 and 7 after administration of the drug.

Experiment 14

Animals and Housing

Sixteen female Sprague-Dawley rats (Samtaco, Osan, Korea) weighing between 180 and 220 g were used. After transportation, the animals were maintained in the central animal laboratory for at least 1 week. The animals were housed in independently ventilated cages and were allowed free access to water and food. The temperature was maintained at $21\pm1°$ C., and the lights were turned on from 8:00 AM to 8:00 PM. Rats with an inner ear infection were not used. This study was approved by the Committee for Ethics in Animal Experiments of the Ajou University School of Medicine.

Experiment 15

Anesthesia and Drug Treatment

Animals were sedated using an intraperitoneal (IP) injection of 3.125 mg/kg xylazine, 3.125 mg/kg zolazepam and 11.5 mg/kg xylazine. The rats were divided into two groups after baseline auditory brainstem response (ABR) testing was performed. Eight rats received 2 mM transtympanic the compound of Example 2 injections in the right ear (cisplatin plus the compound of Example 2 group, eight ears) and saline in the left ear (cisplatin only group, eight ears), followed 30 min later with IP injection of cisplatin (14 mg/kg given as an IP infusion over a 30-min period). The control group (four rats, eight ears) received transtympanic saline in both ears followed by IP saline (16 mL/kg by IP infusion). The compound of Example 2 only group (four rats, eight ears) received transtympanic the compound of Example 2 in both ears followed by IP saline (16 mL/kg by IP infusion). On days 2 to 5, daily transtympanic injections of either 2 mM the compound of Example 2 or saline were continued. Posttreatment ABR was obtained on day 14.

Experiment 16

Auditory Brainstem Responses

Preyer's reflex and otoscopy were used to confirm that the middle ears were normal. The rats were anaesthetized using an IP injection of 3.125 mg/kg zolazepam and 11.5 mg/kg xylazine. Subdermal sterile stainless steel electrode needles were attached, with the active lead at the vertex that referred to a second electrode located at the tip of the nose. The grounding electrode was placed on the front paw muscles. ABR stimuli were generated using a DT Auditory Evoked Potentials Workstation (Tucker-Davis Technologies, Alachua, Fla., USA); 10-ms tone burst stimuli (8 kHz) were delivered monaurally through a hollow rat ear bar. Tone bursts (rise-fall time 2 ms, duration 10 ms) were delivered at the rate of 20 $s^{-1}$, with increasing intensity from 10-80 dB sound-pressure level in 5-dB steps; 10 trials were averaged to assure an adequate brain response. The lowest response that clearly demonstrated a reproducible waveform was interpreted as the threshold response.

Experiment 17

Preparation of Tissues

After fixation by intralabyrinthine perfusion of 4% paraformaldehyde (pH 7.4), the cochleae were removed and then were incubated in the same fixative overnight. Decalcification was performed in ethylenediamine tetraacetic acid solution (EDTA) (10% in PBS) for 3-4 weeks. Subsequently, the tissues were embedded in paraffin.

Experiment 18

Tissue TUNEL Assay

Organ of Corti explants were each fixed for 15 min in 3.7% (v/v) formaldehyde in PBS at room temperature. Each explant was rinsed with PBS and incubated in proteinase K diluted from the TUNEL kit for 15 min at room temperature. After two PBS washes, each explant was incubated with 1× TdT labeling buffer for 2 min. The labeling buffer was drained and labeling reaction mixtures containing labeling buffer, biotin-nucleotide mix and TdT enzyme were added to each explant and incubated in a humid atmosphere at 37° C. for 1 h. The reaction was terminated with 1× TdT stop buffer. Each explant was washed twice with PBS and examined using a fluorescence microscope.

Experiment 19

Cochlea Immunohistochemical Analysis

A LSAB Universal K680 immunohistochemistry kit (DAKO, Carpinteria, Calif., USA) was used according to the manufacturer's instructions. The harvested temporal bone was fixed in 4% paraformaldehyde for 16 h, and then decalcificated with 10% EDTA in PBS for 2 weeks, dehydrated, and embedded in paraffin wax. Sections of 5 m thickness were deparaffinized in xylene and rehydrated through graded concentrations of ethanol. The endogenous peroxidase was blocked with 3% H2O2 for 5 min at room temperature following a PBS wash. Nonspecific binding was blocked with 1% bovine serum albumin for 1 h. Then, anti-NOX3 (Nicotinamide adenine dinucleotide phosphate-oxidase 3) antibody (Sigma-Aldrich) was added to the slides, and incubation proceeded for 1 h. After repeated washes with PBS, the sections were incubated with biotinylated secondary rabbit antibody for 1 h and then covered for 30 min with a secondary antibody containing horseradish peroxidase. Finally, the sections were stained in a freshly prepared substrate solution (3 mg of 3-amino-9-ethylcarbazole in 10 ml of sodium acetate buffer pH 4.9, 10 L of dimethylformamide, 0.03% H2O2) for 10 min.

The results of the above-mentioned Examples and Experiments are as follows.

Figure 2B:
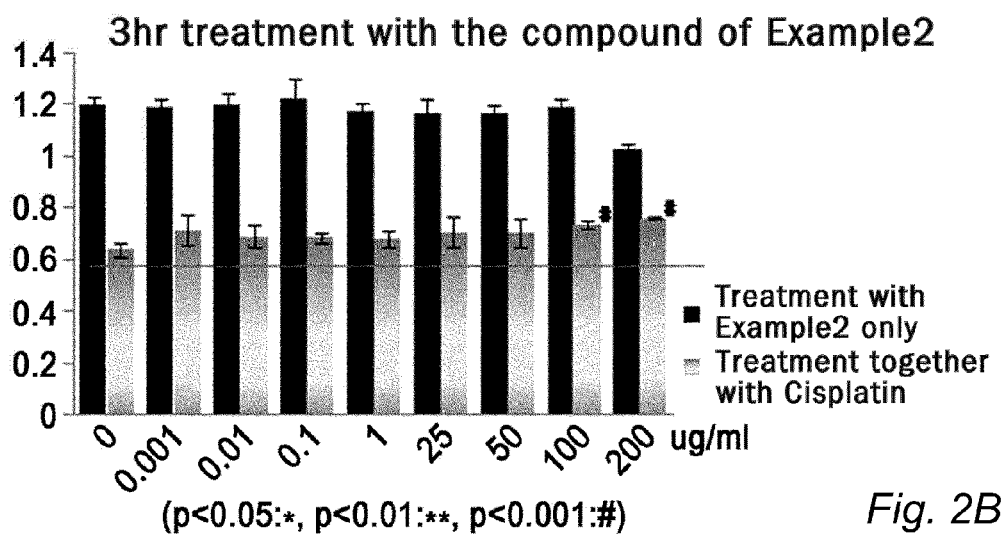

(1) Analysis of the Efficacy in Inhibiting Apoptosis of Auditory Cells Induced by Ototoxic Anti-Cancer Agent, Cisplatin, with MTT Assay The cytotoxicity of the compound of Example 1 in auditory hair cells (HEI-OC1 (FIGS. 1A and 1B), UB-OC1 (FIGS. 1C and 1D) was demonstrated with MTT assay. As a result, it has been identified that the compound of Example 1 has substantially no cytotoxicity even at the elevated dose of 200. According to the result of analysis through MTT assay for apoptosis of auditory cells induced by cisplatin, a typical anti-cancer agent inducing apoptosis, it has been identified that 50 of cisplatin kills about 50% of auditory hair cells HEI-OC1 and UB-OC1, and the apoptosis of auditory hair cells was statistically significantly inhibited by treatment with the compound of Example 1 as the dose of the compound increases. In addition, the substantially same result was also identified for the compound of Example 2 (FIGS. 2A-2B).

Figure 3A:
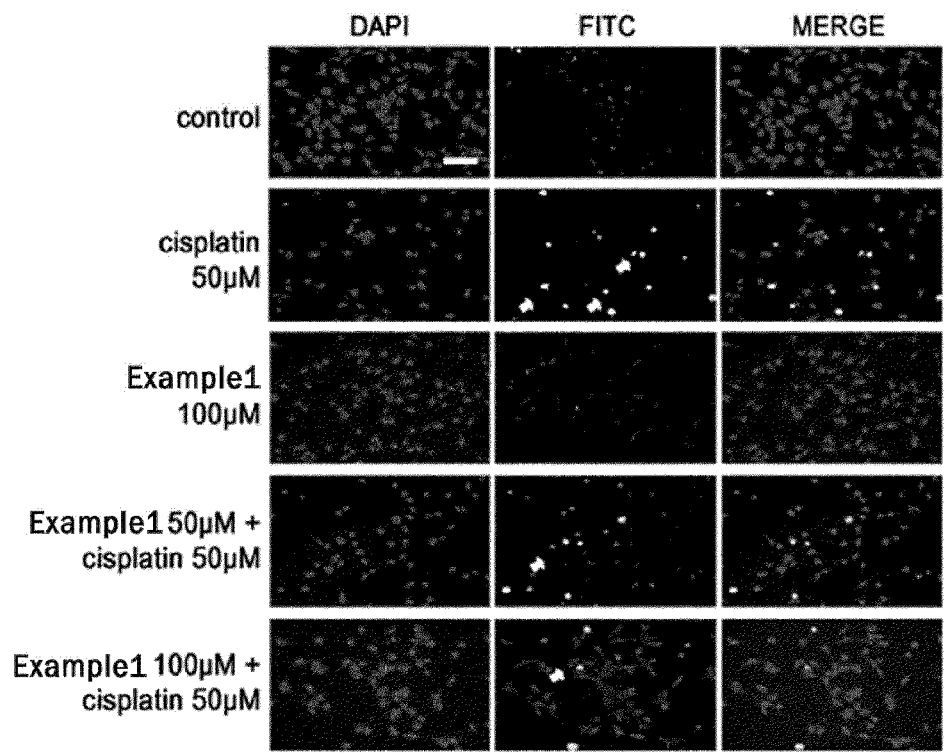
FIG. 3A-3B shows the result of TUNEL assay for the effect of the compound of the Example 1 to inhibit apoptosis of auditory cells induced by anti-cancer agent, cisplatin, as the ototoxic material.
Figure 3B:
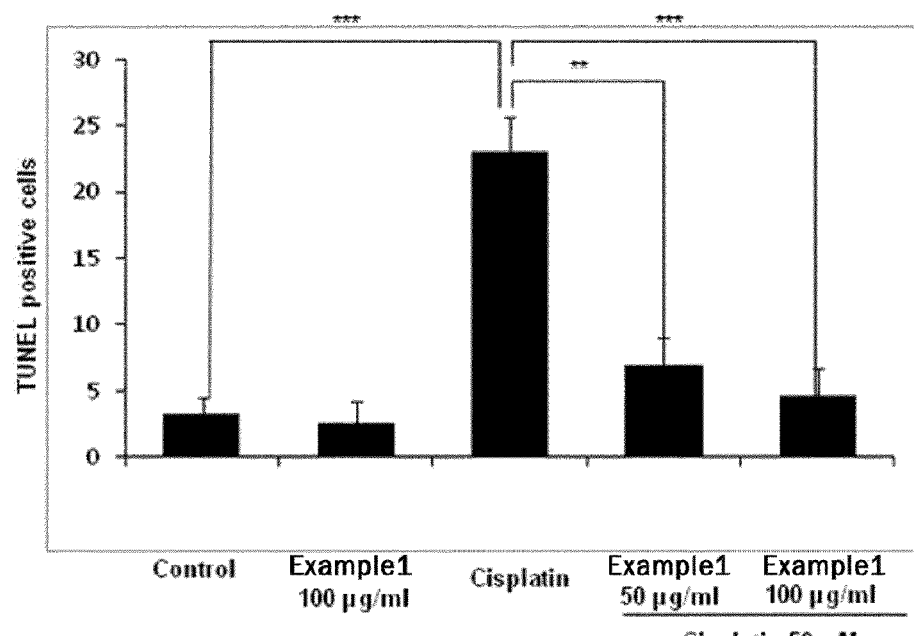
Figure 3C:
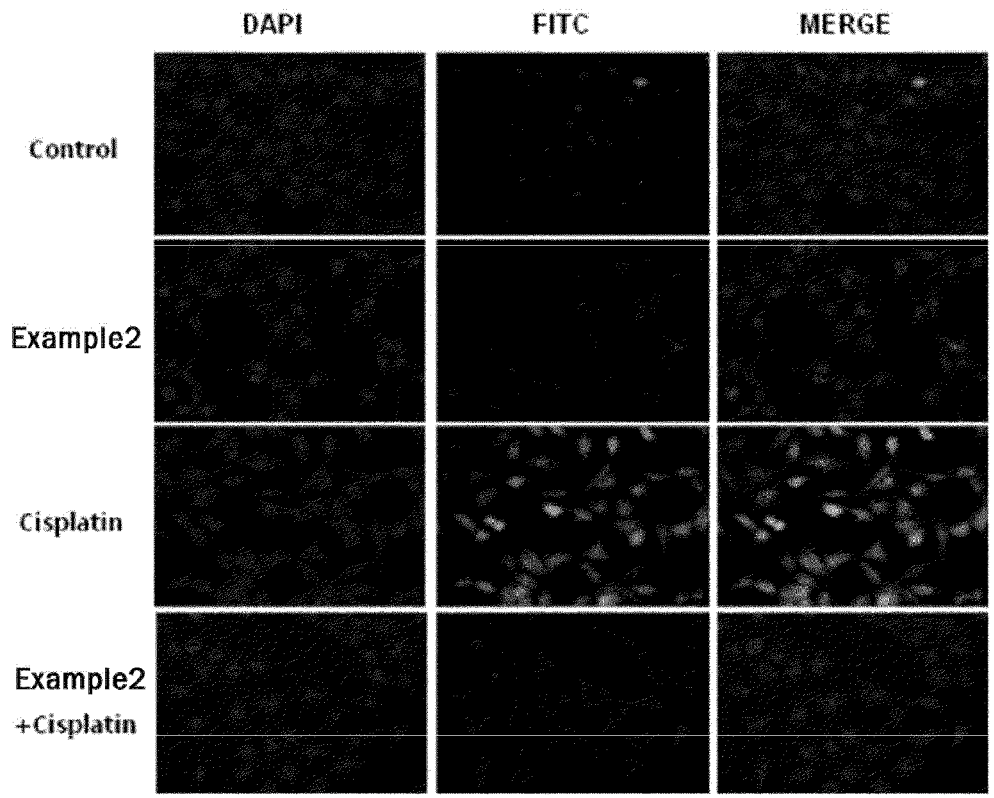
FIGS. 3C-3D shows the result of TUNEL assay for the effect of the compound of the Example 2 to inhibit apoptosis of auditory cells induced by anti-cancer agent, cisplatin, as the ototoxic material.
Figure 3D:
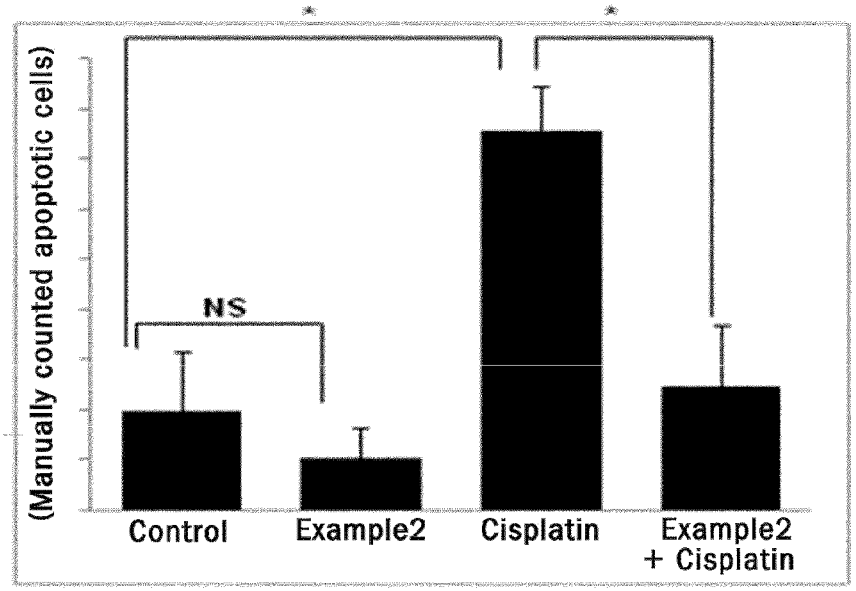

(2) Analysis of the Efficacy in Inhibiting Apoptosis of Auditory Cells Induced by Cisplatin, with TUNEL Assay It has been identified that TUNEL positive cells reflecting apoptosis increased by treatment of auditory cells with 50 μM of cisplatin, and administration of the compound of Example 1 alone did not cause apoptosis (FIGS. 3A and 3B). Further, it has been identified that TUNEL positive cells reflecting apoptosis increased by treatment of auditory cells with 20 μM of cisplatin, and administration of the compound of Example 2 alone did not cause apoptosis (FIGS. 3C and 3D). When cisplatin and the compound of Example 1 or the compound of Example 2 were administered at the same time in order to observe the auditory protective effect of the compound of Example 1 or the compound of Example 2 against cisplatin, it could be identified that the apoptosis of auditory cells was inhibited. See FIGS. 3A-3D.

Further, it has been also identified that treatment with 100 μM of the compound of Example 1 provides a better effect as compared to treatment with 50 μM of the compound of Example 1, in a dose-dependent manner (FIGS. 3A and 3B).

Figure 4A:
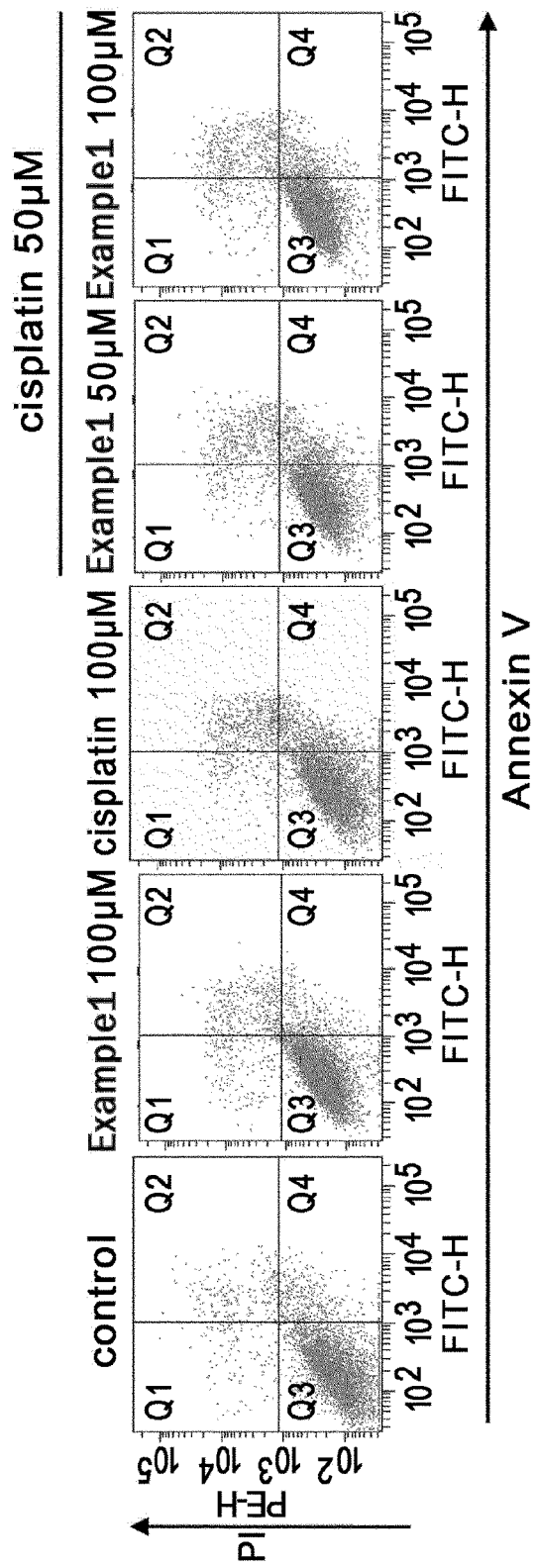
FIGS. 4A-4B show the results of annexin and PI double staining and then FACS analysis for the effect of the compound of Example 1 to inhibit apoptosis of auditory cells induced by anti-cancer agent, cisplatin, as the ototoxic material.
Figure 4B:
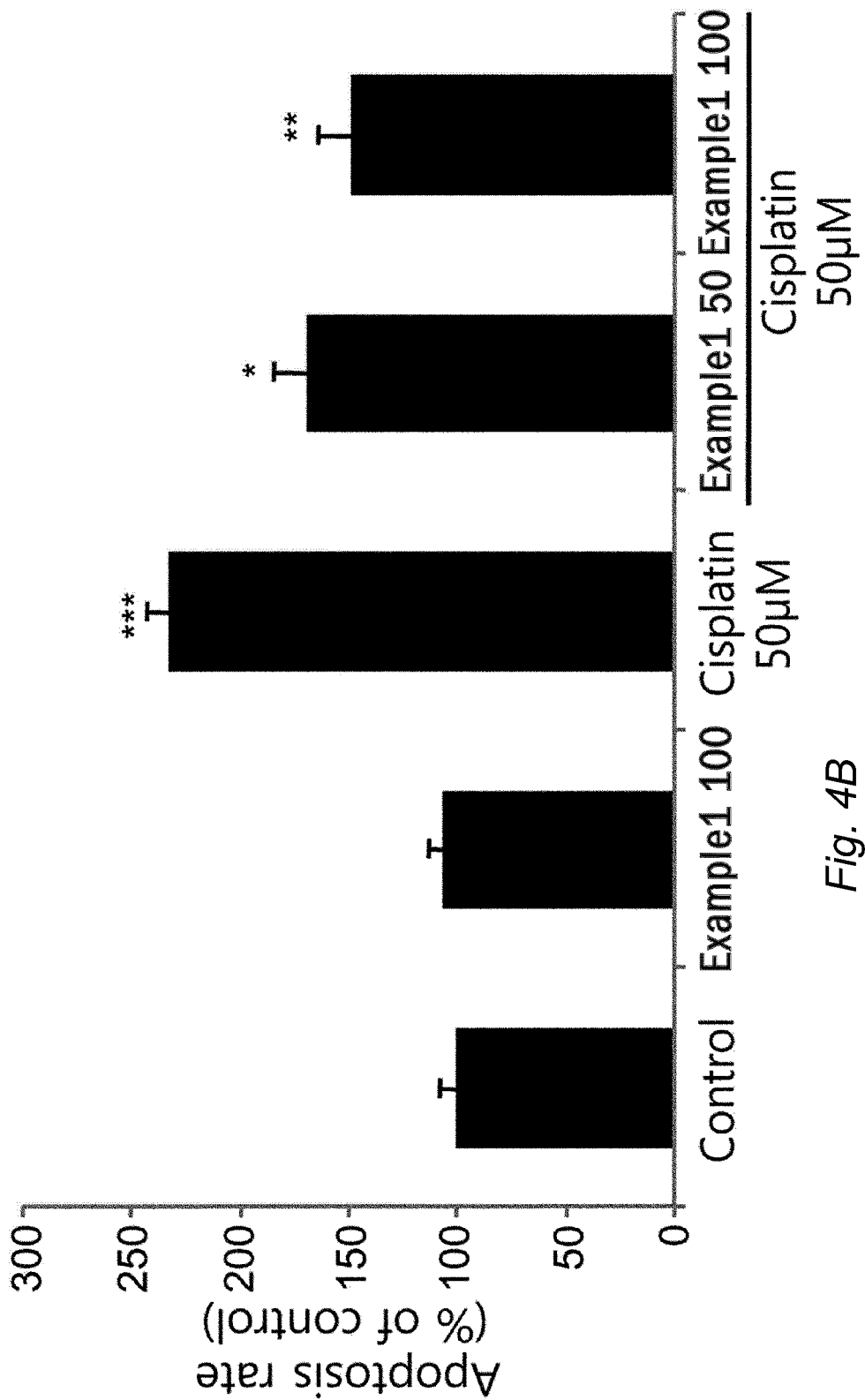
Figure 5A:
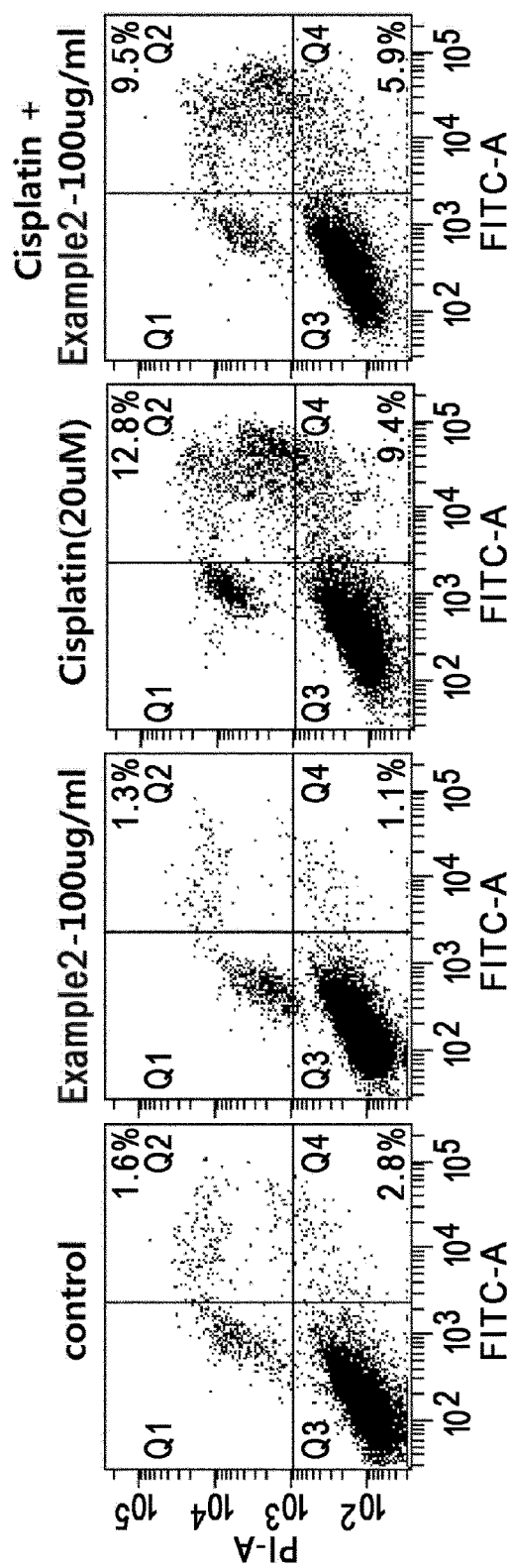
FIGS. 5A-5B show the results of annexin and PI double staining and then FACS analysis for the effect of the compound of Example 2 to inhibit apoptosis of auditory cells induced by anti-cancer agent, cisplatin, as the ototoxic material.
Figure 5B:
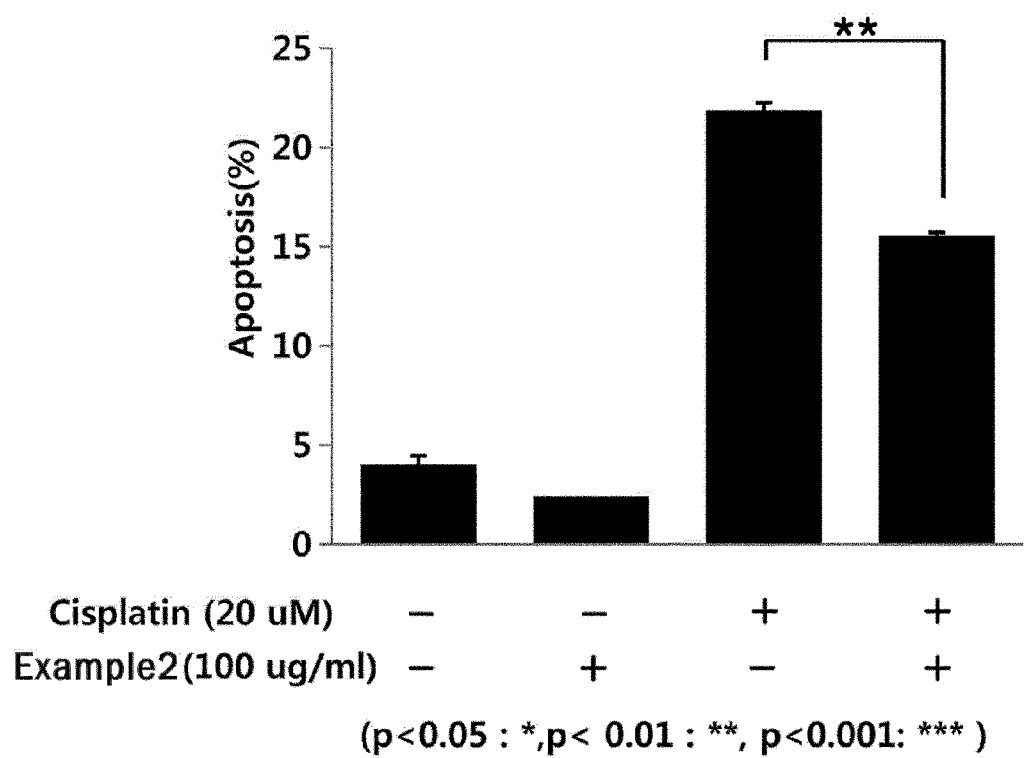

(3) Analysis of the Efficacy in Inhibiting Apoptosis of Auditory Cells Induced by Cisplatin, with FACS To identify the protective effect of the compounds of Examples 1 and 2 against apoptosis of auditory cells induced by cisplatin, auditory cells were double stained with annexin and PI, and then analyzed with FACS. As a result, it could be identified that the apoptosis increased by 50 μM of cisplatin was statistically significantly inhibited by simultaneous administration of the compound of Example 1 (FIGS. 4A-4B) or 2 (FIGS. 5A-5B). Further, it has been also identified that treatment with 100 μM of the compound of Example 1 provides a better effect as compared to treatment with 50 μM of the compound of Example 1, in a dose-dependent manner (FIG. 4B).

(4) FACS Analysis for the Effect on Cell Cycle

Figure 6A:
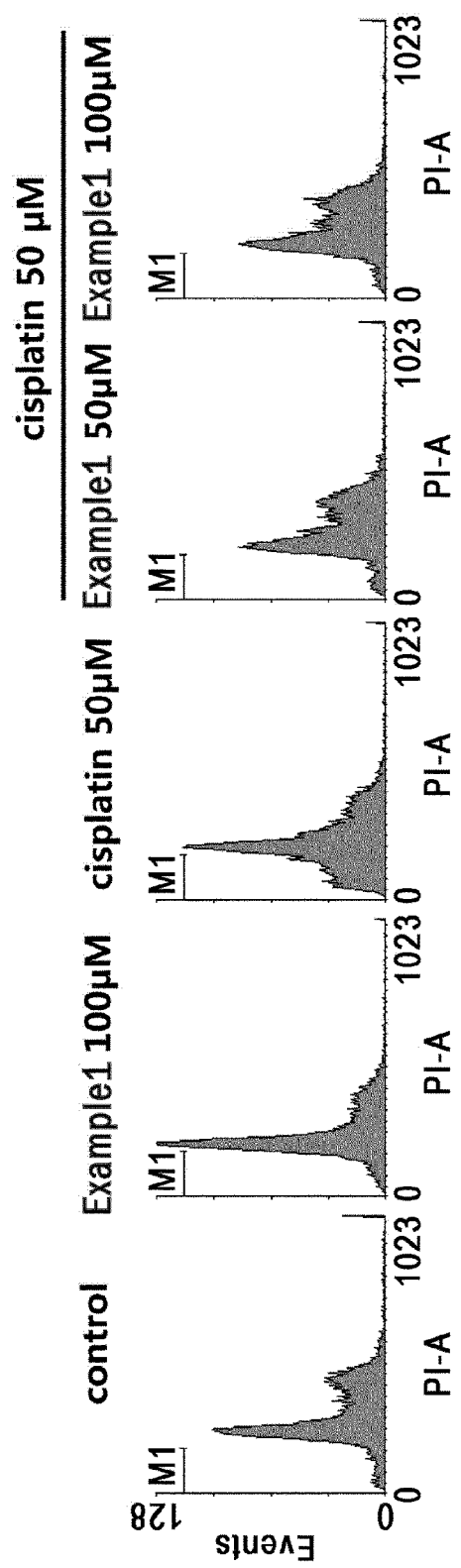
FIG. 6A-6B shows the results of cell cycle analysis for the effect of the compound of the present invention to inhibit apoptosis of auditory cells induced by anti-cancer agent, cisplatin, as the ototoxic material.
Figure 6B:
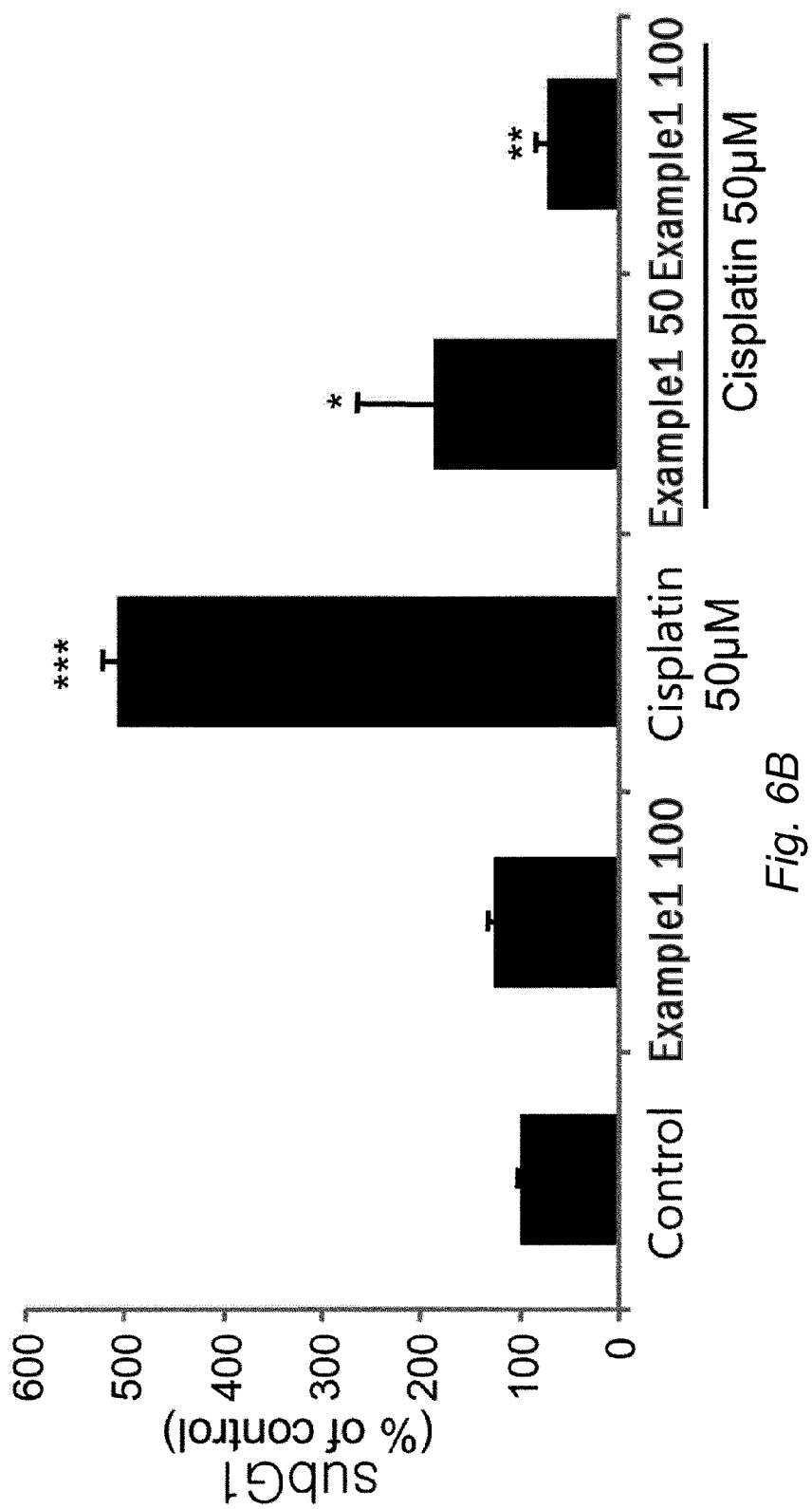

To identify the effect of the compound of Example 1 on cell cycle any change in sub G1 related to apoptosis was confirmed. It could be identified that an increase in sub G1 induced by cisplatin was effectively reduced by treatment with the compound of example 1 (FIG. 6A-6B).

(5) Analysis of the Effect on Mitochondrial Membrane Potential

Figure 7A:
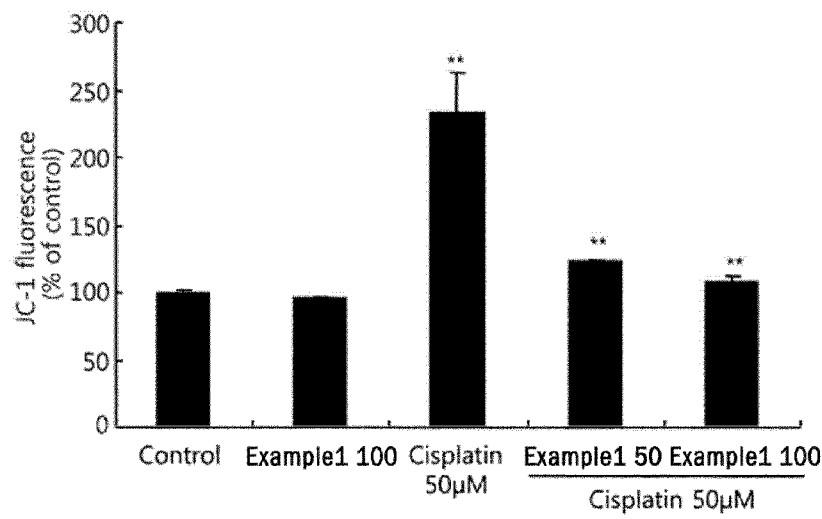
FIGS. 7A-7B show the results of analysis for the effect of the compound of the Example 1 on a change in the mitochondrial membrane potential of auditory cells induced by anti-cancer agent, cisplatin, as the ototoxic material.
Figure 7B:
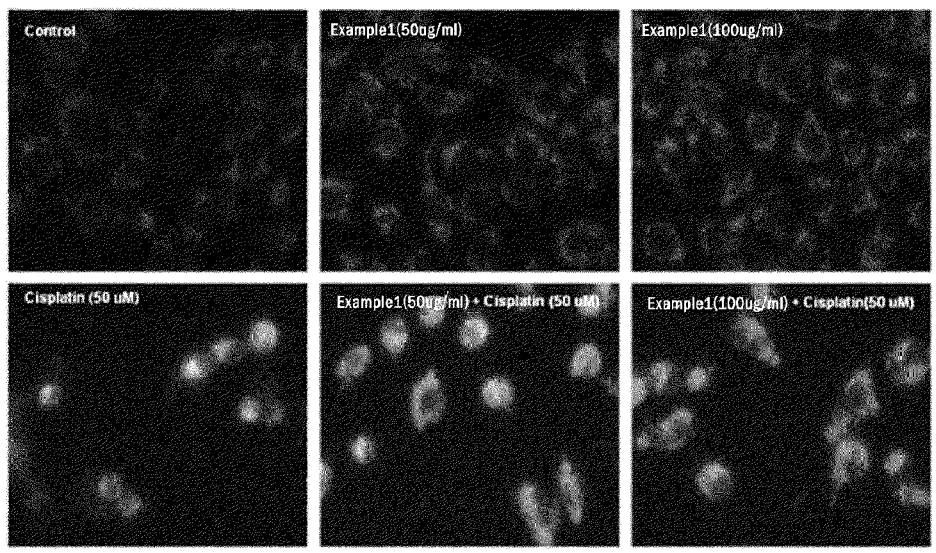
Figure 8A:
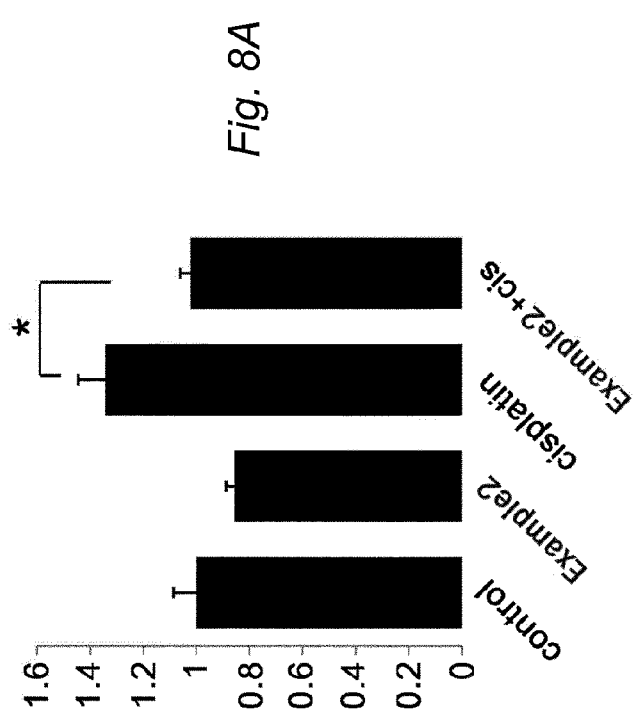
FIGS. 8A-8B show the results of analysis for the effect of the compound of the Example 2 on a change in the mitochondrial membrane potential of auditory cells induced by anti-cancer agent, cisplatin, as the ototoxic material.
Figure 8B:
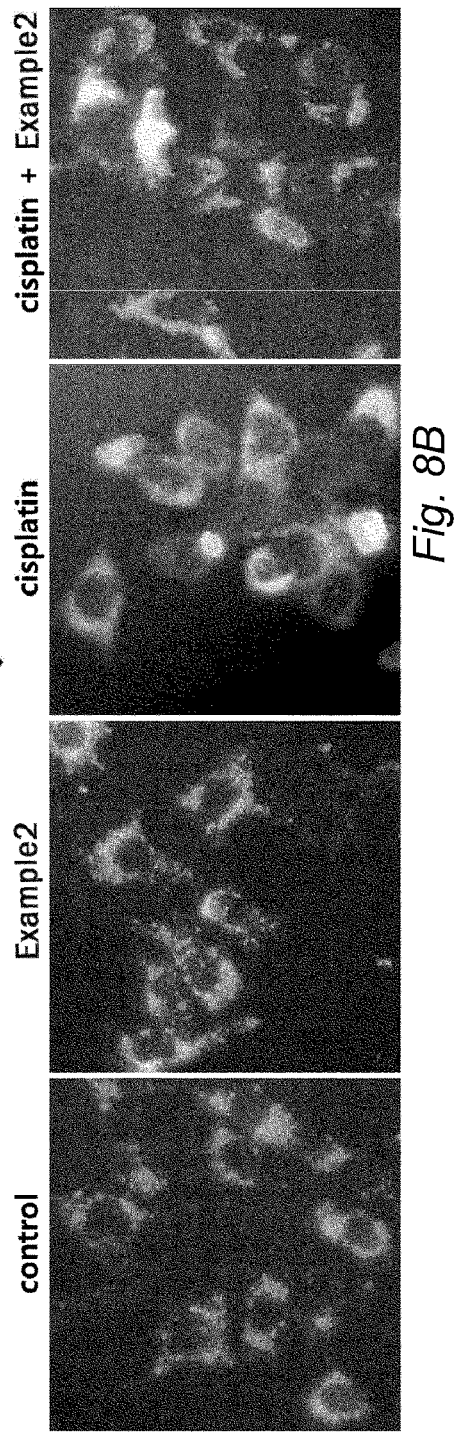

For measurement of the damage of mitochondria as one of important mechanisms of apoptosis, the mitochondrial membrane potential (MMP) was measured to identify the protective effect of the compounds of Examples 1 and 2 against mitochondria damage caused by cisplatin. As a result, it could be identified that HEI-OC1 cells of the normal control group remains red with maintaining high MMP, but by treatment with cisplatin was changed into green fluorescence thereby identifying the damage of mitochondria, and that such phenomenon was inhibited by the compounds of Examples 1 (FIGS. 7A-7B) and 2 (FIGS. 8A-8B)

(6) Apoptosis Mechanism Inhibited by the Compound of the Present Invention

Figure 9:
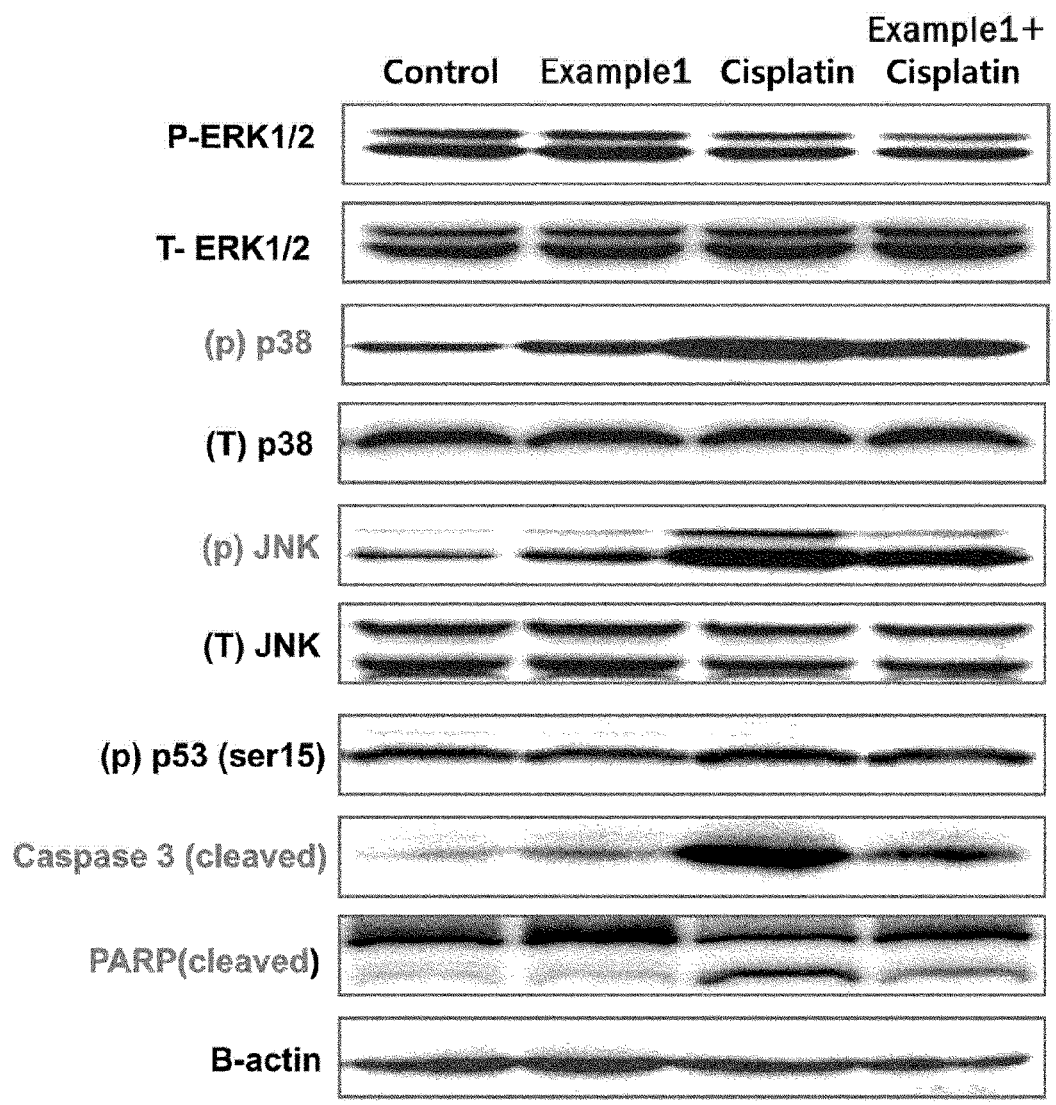
FIG. 9 show the results of Western blot analysis for the effect of the compound of the Example 1 on a change I auditory cell apoptosis-related genes (ERK, p38, JNK, p53, caspase 3, PARP) induced by anti-cancer agent, cisplatin, as the ototoxic material.
Figure 10:
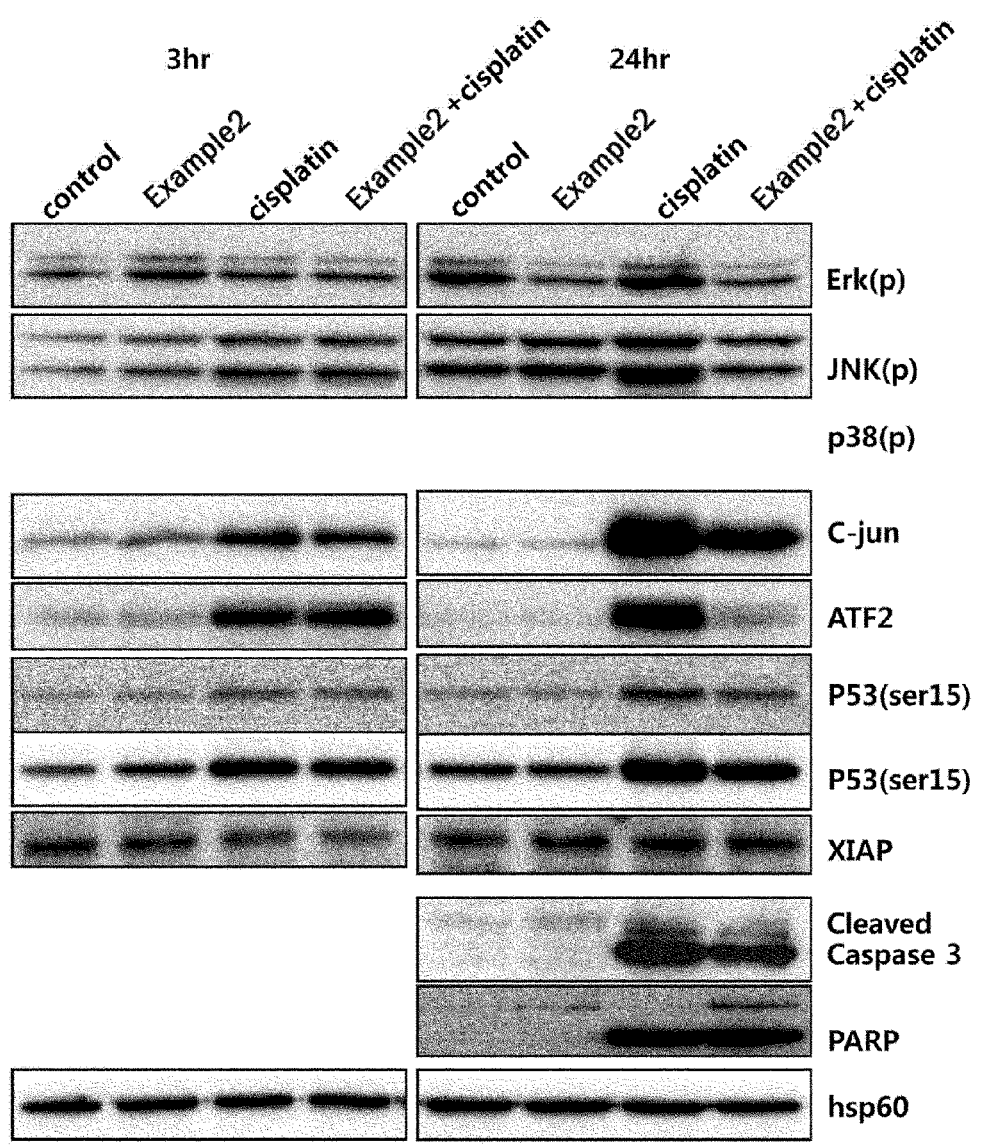
FIG. 10 show the results of Western blot analysis for the effect of the compound of the Example 2 on a change I auditory cell apoptosis-related genes (ERK, p38, JNK, p53, caspase 3, PARP) induced by anti-cancer agent, cisplatin, as the ototoxic material.

In Western blot assay practiced to study the mechanism of the compounds of Examples 1 and 2, it has been identified that JNK, p38, cleaved caspase 3, PARP were increased by cisplatin and then, effectively inhibited by the compounds of Examples 1 and 2, and thus that the compounds of Examples 1 (FIG. 9) and 2 are involved in the apoptosis mechanism to inhibit apoptosis (FIG. 10).

Figure 11A:
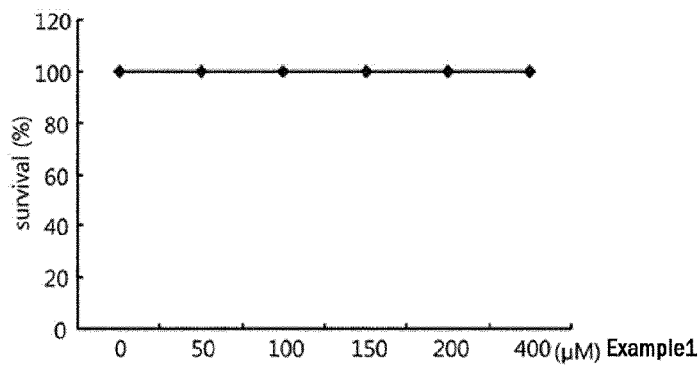
FIG. 11A shows the result of the embryotoxicity test using zebrafish model as the test for toxicity of the compound of Example 1 of the present invention.
Figure 11B:
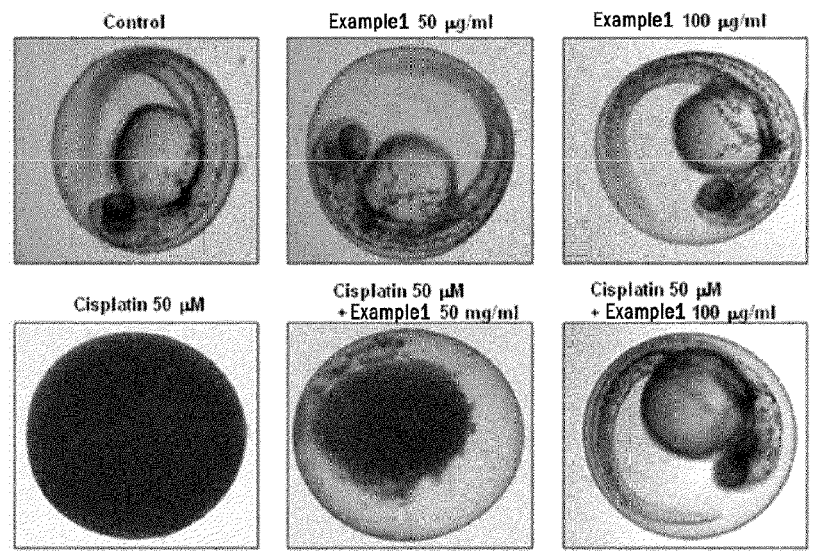
FIG. 11B shows the results of Zebrafish embryos that were treated with various concentrations of the compound of Example 1 (0, 50, 100 μg/ml) only or cisplatin (50 μM) plus the compound of Example 1 for 24 h.
Figure 11C:
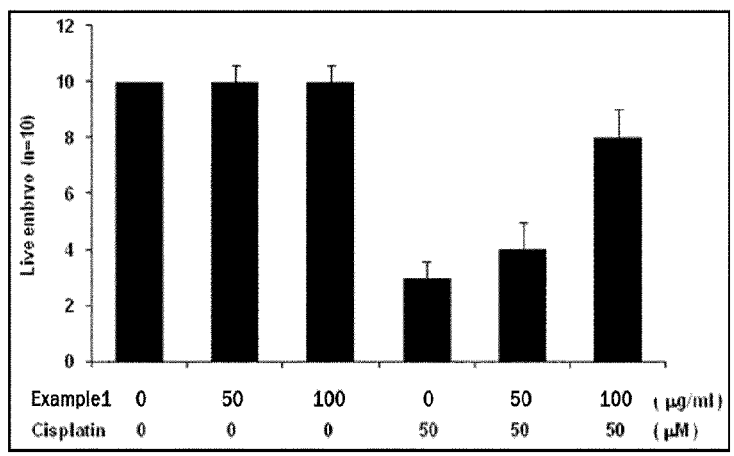
FIG. 11C shows the number of live embryos after the treatment of the compound of Example 1 with/without ciplatin.

(7) Study of Toxicity of the Compound of the Present Invention and Protective Effect for Embryos and Hair Cells of Zebrafish from Cisplatin Toxicity As the result of the test for embryotoxicity of the compound of the present invention, as the toxicity test, using zebrafish model, the compound of Example 1 did not show the drug toxicity even at the concentration of 400 μM. In addition, as the result of identification of the drug toxicity for 7 days after incubation of zebrafish, the compound of Example 1 did not show the drug toxicity at any of the concentration of 50, 100, 150, 200, 400 μM (FIG. 11A). Further, the compound of Example 1 treatment rescued the zebrafish embryos from the damage caused by cisplatin (50 μM) (FIGS. 11B-11C).

Figure 13A:
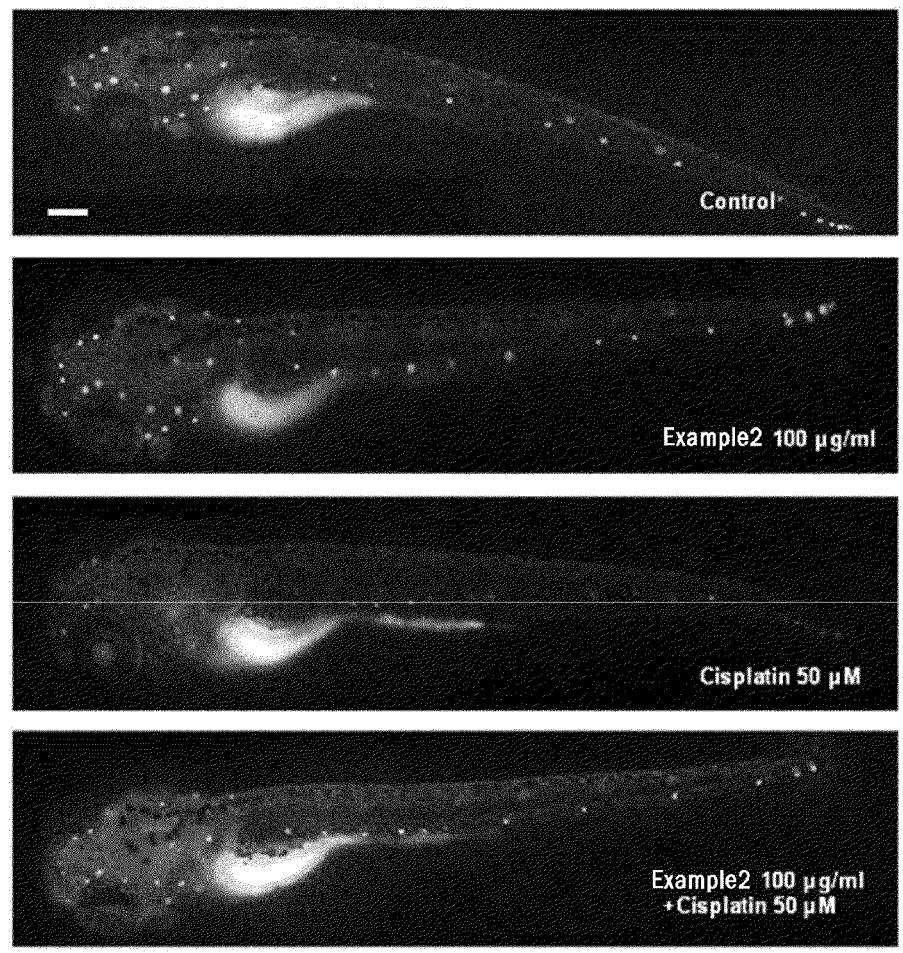
FIGS. 13A-13B are photographs obtained from fluorescence microscopy for the auditory protective effect using zebrafish model for the compound of Example 2.
Figure 13B:
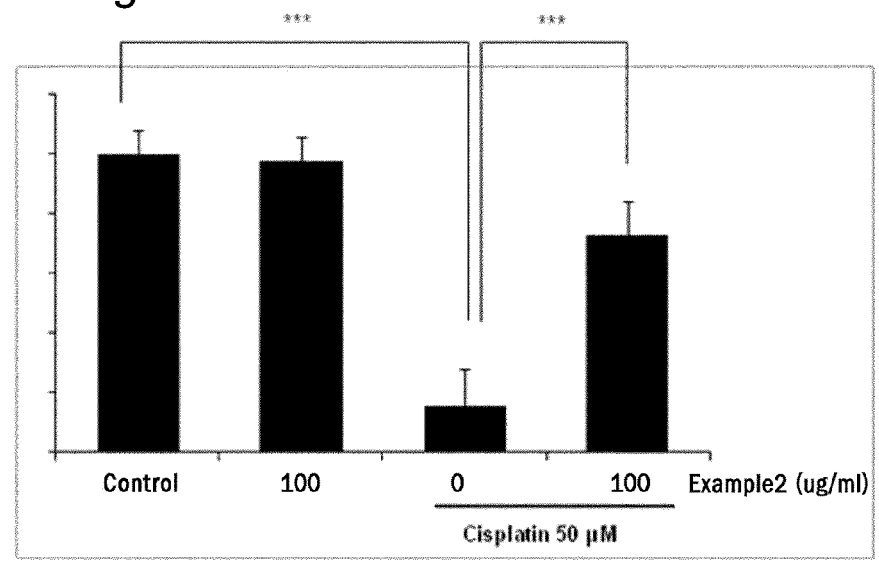

(8) Analysis of the Auditory Protective Effect of the Compound of the Present Invention in Zebrafish From in vivo experiment using zebrafish, the photographs were obtained by staining neuromast, as the sensory nerve system including auditory hair cells of zebrafish on the 4th day after incubation, with YO-PRO1. As can be seen from the photographs, it was observed that in case of cisplatin treatment neuromast was reduced from the initial dose with being reduced by 70% or more in case of treatment with 50 μM cisplatin, and substantially all of neuromast was disappeared in case of treatment with 100 μM cisplatin. Further, it could be identified that neuromast including auditory hair cells, which were disappeared by cisplatin, was effectively protected by the compound of Examples 1 (FIGS. 12A-12B) and 2, and such protective effect was taken in a dose-dependent manner (FIGS. 13A-13B).

Figure 14:
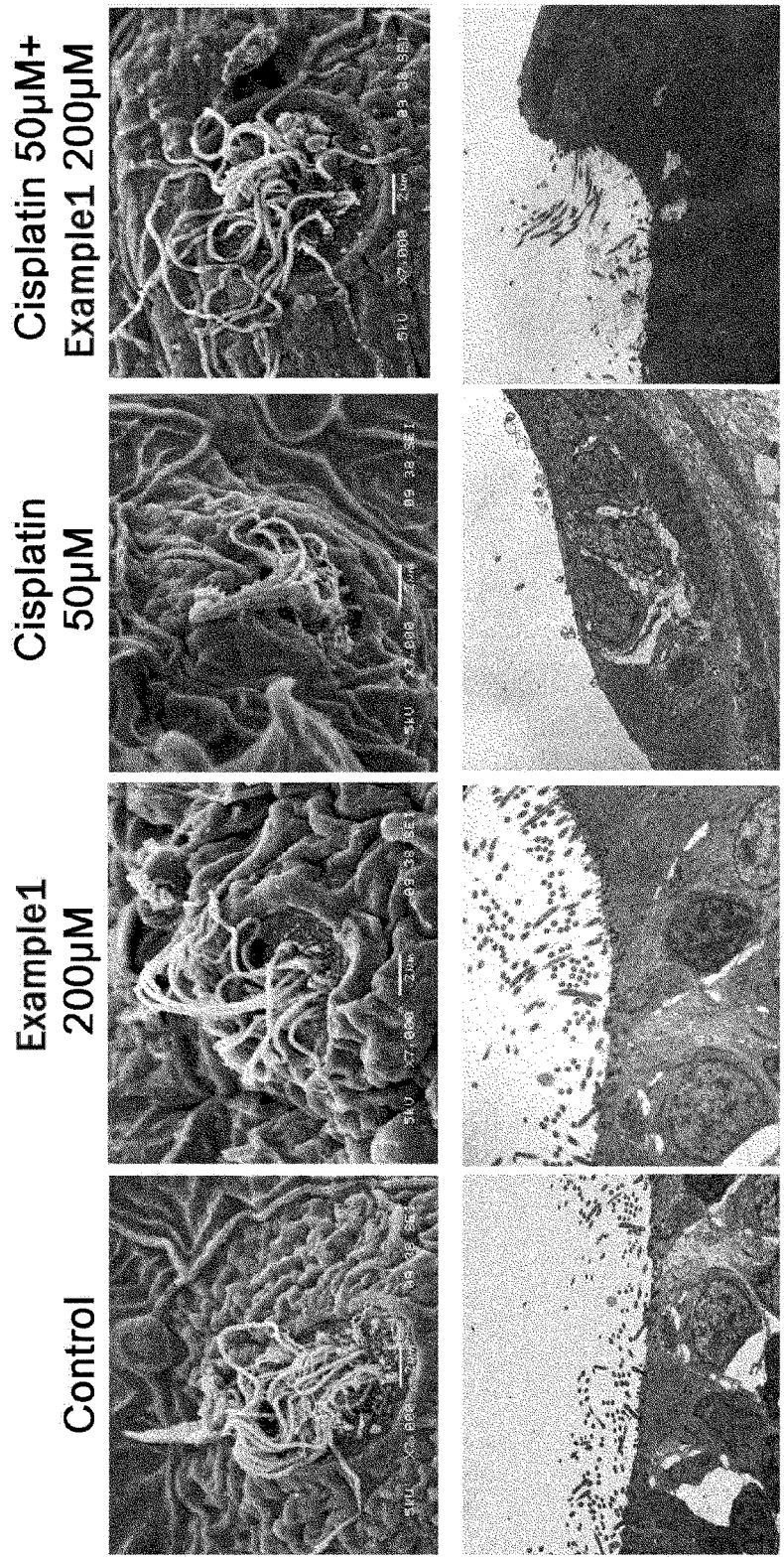
FIG. 14 is the photographs obtained from scanning electron microscopy and transmission electron microscopy for auditory protective effect using zebrafish model.
Figures 16A, 16B, 16C, 16D:
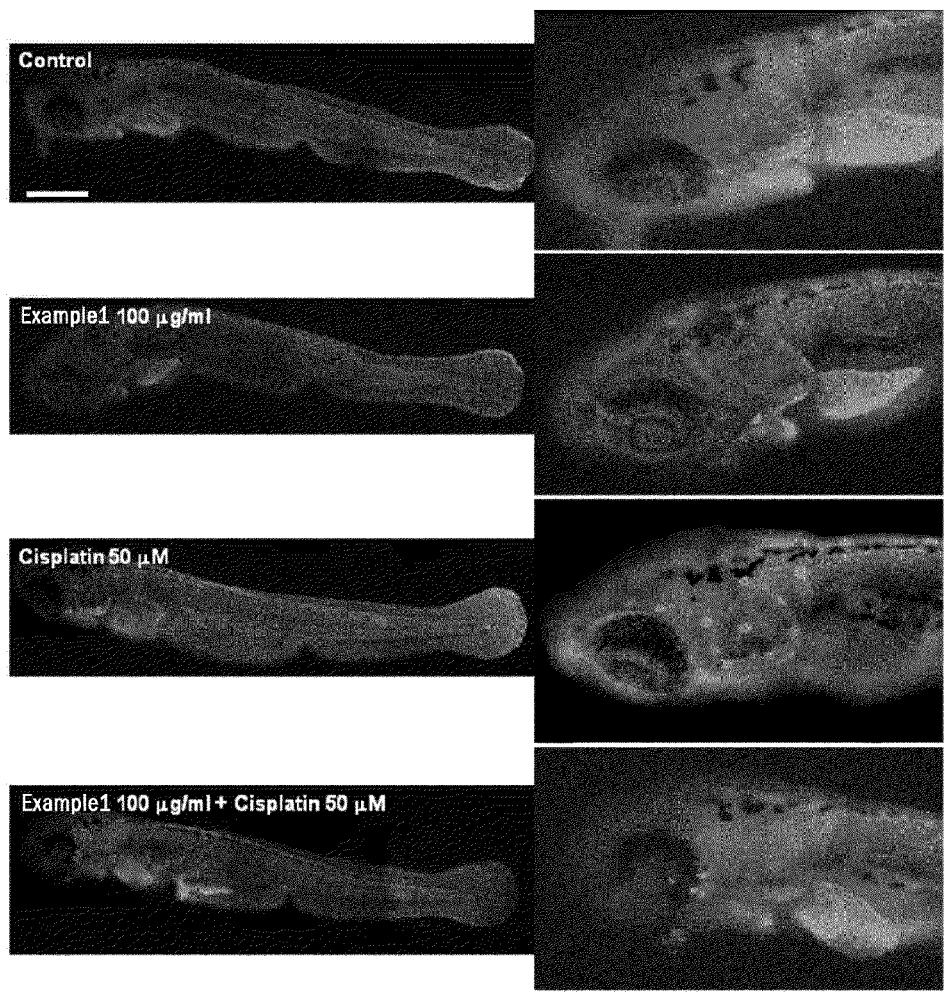
FIGS. 16A-16D is the apoptotic signals on 4 dpf larvae obtained by TUNEL assay and recorded using a fluorescence microscope. Fluorescence signals of zebrafish larvae were treated with (FIG. 16A) media only, (FIG. 16B) 100 μg/ml the compound of Example 1, (FIG. 16C) 50 μM cisplatin, and (FIG. 16D) 50 μM cisplatin+100 μg/ml the compound of Example 1 for 1 h. Right panel represents magnified pictures of white box in left panel. Scale bar=50 μm.

(9) Analysis with Scanning and Transmission Electron Microscopy (SEM, TEM) for Zebrafish Neuromast From the result of scanning and transmission electron microscopy conducted in order to morphologically identify a change in microstructure for zebrafish neuromast protective effect of the compound of Example 1 as observed under fluorescent microscope, it could be observed that kinocilium of auditory cells of neuromast, which was well identified under normal condition, was markedly damaged or mostly disappeared or fused in case of treatment with 50 μM cisplatin, but the combined use of the compound of Example 1 inhibited the damage of kinocilium and stereocilia caused by cisplatin to protect the auditory organs (FIG. 14).

(10) Analysis of Decreasing Effect of the Compound of the Present Invention on Cisplatin-Induced ROS Treatment with cisplatin significantly increased the generation of intracellular ROS in a time-dependent manner. The compound of Example 1 and the compound of Example 2 significantly inhibited cisplatin-induced intracellular ROS generation, suggesting that those compounds might prevent HEI-OC1 cells from cisplatin toxicity through reduction of intracellular ROS formation (FIGS. 15A-C).

(11) Cisplatin-Induced Apoptosis was Inhibited by the Compound of Example 1 Pretreatment In Vivo in Neuromasts of Zebrafish To assess in vivo apoptotic death of zebrafish neuromasts, tissue TUNEL staining was performed in 4 dpf zebrafish larvae. Exposure to 50 μM cisplatin for 24 h resulted in increased TUNEL positive cells. However, co-treatment with the compound of Example 1 reduced TUNEL positive cells compared to treatment with cisplatin alone. Those results suggest that cisplatin promotes apoptotic cell death in neuromasts of zebrafish and indicate that cisplatin-induced apoptosis could be inhibited by the compound of Example 1 pretreatment in vivo (FIGS. 16A-16D).

(12) Measurement of Brainstem Evoked Potential in Rat for Evaluation of Auditory Protective Effect From the preceding cell experiments and the experiments using zebrafish, it could be identified that the compound of the present invention protects the auditory organs to be damaged by cisplatin. Thus, in order to identify whether the auditory organs can be functionally protected, it was demonstrated in rats whether the hearing to be reduced by cisplatin can be protected by treatment with the compound of the present invention.

Figure 17:
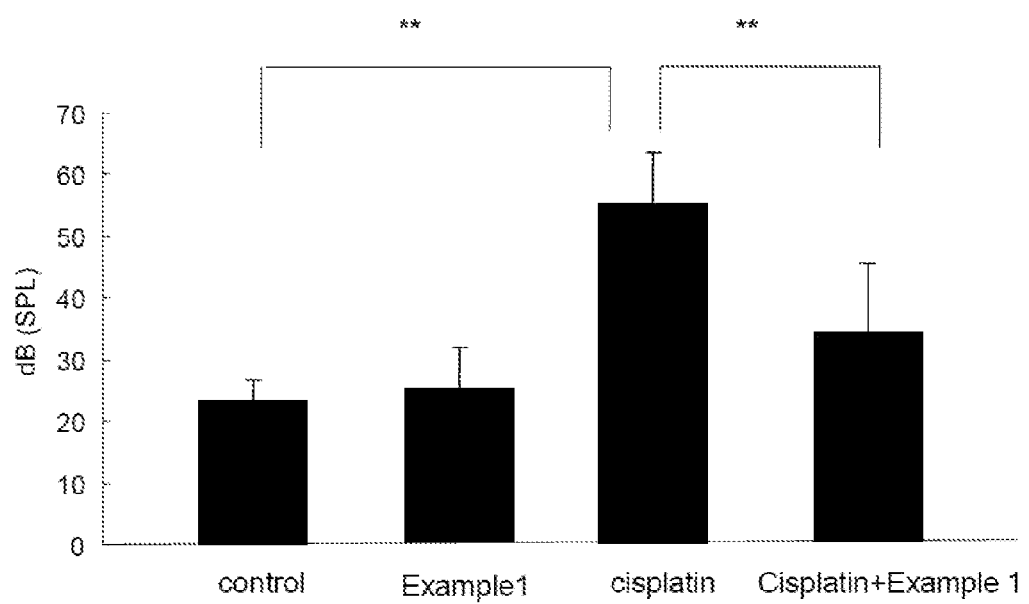
FIG. 17 is a graph showing the result of ABR (Auditory brainstem responses) measurement for auditory protective effect of the compound of the present invention using rat.

As the result of measurement of brainstem evoked potential hearing under neat condition, rats responded to the sound from 75 dB to 15~20 dB. In the group treated with cisplatin only, the hearing threshold was increased to 50~65 dB, but in the group treated with cisplatin in combination with the compound of Example 1 the hearing threshold was reduced to 25~35 dB, which did not show a great difference from the control group showing the hearing threshold of 15~25 dB (FIG. 17).

(13) Transtympanic Injections of the Compound of Example 2 Inhibits Cisplatin-Induced Apoptosis in the Cochlea.

Figure 18:
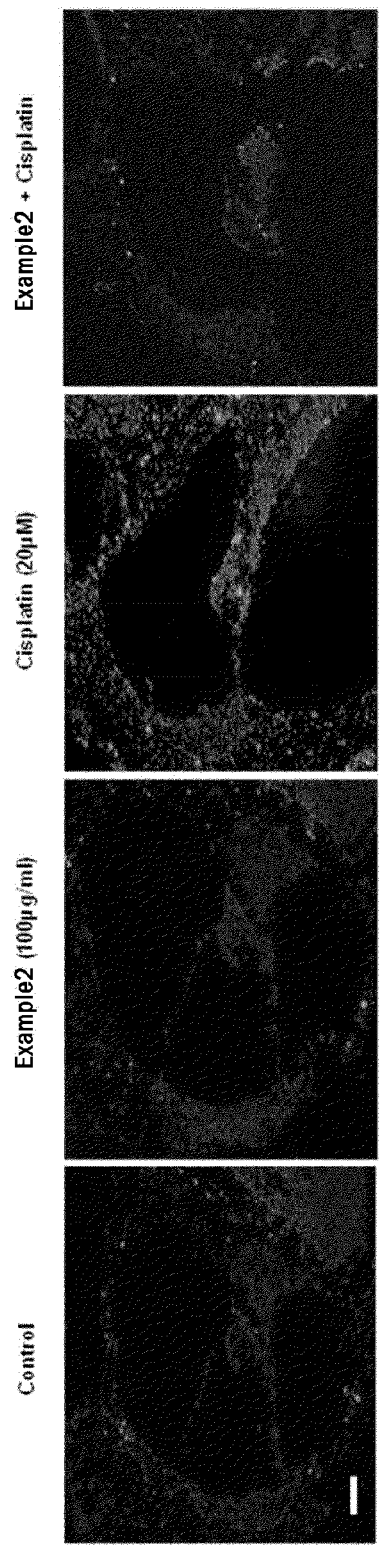
FIG. 18 is the protective effect against cisplatin by the compound of Example 2 treatment in rat cochlea, as indicated by TUNEL staining for apoptosis. Five micrometer-thick cochlear sections from each experimental group were stained using TUNEL (green fluorescence) and then observed using fluorescence microscopy. Scale bar: 50 μm.

Histological sections from cisplatin-only treated rats exhibited TUNEL-positive cells in the stria vascularis, spiral ligament, spiral limbus, and the organ of Corti. TUNEL positive cells were more numerous in the cisplatin only group than the control group, and the numbers of TUNEL positive cells in the cisplatin plus the compound of Example 2 treatment groups were lower than the cisplatin only group (FIG. 18).

(14) Transtympanic Injections of the Compound of Example 2 Reduce Cisplatin-Induced Hearing Loss.

Figure 19:
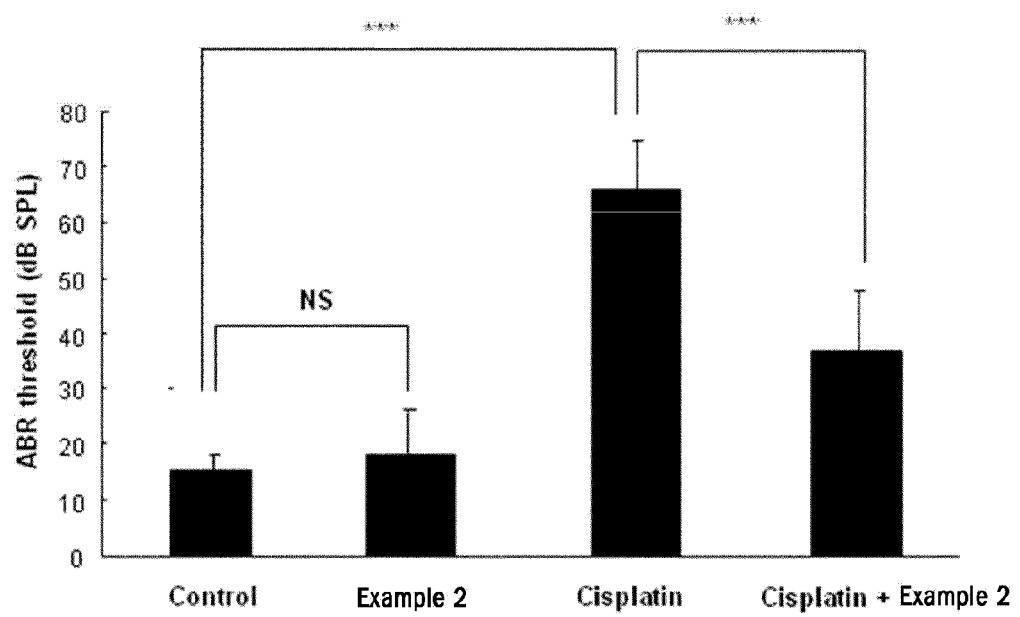
FIG. 19 is the transtympanic injections of the compound of Example 2 reduce cisplatin-induced hearing loss. Auditory brainstem response of treated rats. The cisplatin treatment group (eight rats, sixteen ears) received 2 mM transtympanic the compound of Example 2 in the right ear (the compound of Example 2 treatment group) and saline in the left ear (cisplatin only group), before cisplatin treatment. The control group (four rats, eight ears) and the compound of Example 2 only group (four rats, eight ears) received transtympanic saline or the compound of Example 2 in both ears respectively. NS; Not significant, ***p<0.001

Ears treated with cisplatin had an average click-evoked ABR threshold shift that was 67.3±9.5 dB (range, 57-76 dB), whereas ears pretreated with transtympanic the compound of Example 2 had a minimal average click-evoked ABR threshold shift of 38.5±11.3 dB (range, 27-49 dB). The ABR threshold in the compound of Example 2 treatment group was significantly lower than the cisplatin only group ($p<0.01$), suggesting that the compound of Example 2 had an otoprotective effect in the rats given cisplatin (FIG. 19).

The invention claimed is:

1. A compound or a pharmaceutically acceptable salt thereof, wherein the compound is
   3-amino-3-(4-fluorophenyl)quinolin-2,4(1H,3H)-dione, or
   3-amino-5-fluoro-3-(4-fluorophenyl)quinolin-2,4(1H, 3H)-dione.

2. A method for preparation of the compound according to claim 1, comprising:
   1) reacting a compound represented by the following formula 2 with 2-(4-fluorophenyl)acetyl chloride to prepare a compound represented by the following formula 3;
   2) reacting the compound represented by the following formula 3 with NaH to prepare a compound represented by the following formula 4;
   3) reacting the compound represented by the following formula 4 with $SO_2Cl_2$ to prepare a compound represented by the following formula 5;
   4) reacting the compound represented by the following formula 5 with $NaN_3$ to prepare a compound represented by the following formula 6; and
   5) reacting the compound represented by the following formula 6 with $H_2$ to prepare the compound according to claim 1

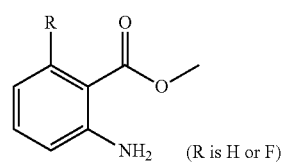

[Formula 2]

(R is H or F)

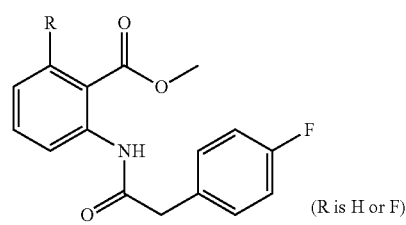

[Formula 3]

(R is H or F)

[Formula 4]

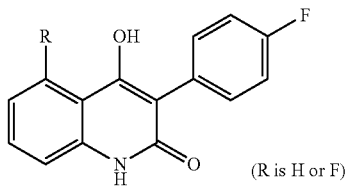

(R is H or F)

[Formula 5]

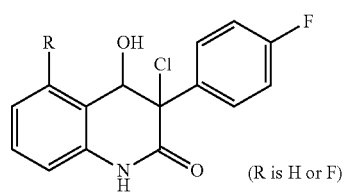

(R is H or F)

[Formula 6]

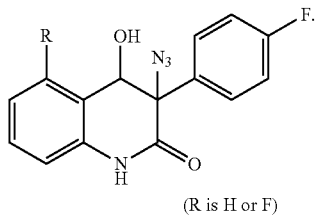

(R is H or F)

3. The method according to claim 2 characterized in that in said step 5) the reaction is carried out under Pd/C catalyst.

4. A pharmaceutical composition comprising the compound according to claim 1 or a pharmaceutically acceptable salt thereof.

5. A health food composition comprising the compound according to claim 1 or a pharmaceutically acceptable salt thereof.

* * * * *